US010067074B2

(12) United States Patent
Quintanilha et al.

(10) Patent No.: US 10,067,074 B2
(45) Date of Patent: Sep. 4, 2018

(54) METROLOGY METHODS, METROLOGY APPARATUS AND DEVICE MANUFACTURING METHOD

(71) Applicant: ASML Netherlands B.V., Veldhoven (NL)

(72) Inventors: Richard Quintanilha, Eindhoven (NL); Serhiy Danylyuk, Jülich (DE)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/079,860

(22) Filed: Mar. 24, 2016

(65) Prior Publication Data

US 2016/0282282 A1    Sep. 29, 2016

(30) Foreign Application Priority Data

Mar. 25, 2015  (EP) .................................... 15160786

(51) Int. Cl.
  *G06K 9/00* (2006.01)
  *G01N 21/956* (2006.01)
  (Continued)

(52) U.S. Cl.
  CPC ....... *G01N 21/956* (2013.01); *G01N 21/8806* (2013.01); *G03F 7/2004* (2013.01);
  (Continued)

(58) Field of Classification Search
  CPC ............. G03F 7/70625; G03F 7/70608; G03F 7/7065; G03F 9/7088; G03F 9/7092;
  (Continued)

(56) References Cited

U.S. PATENT DOCUMENTS 6,180,415 B1 * 1/2001 Schultz .................. B82Y 30/00
                                                         356/301
6,657,736 B1   12/2003 Finarov et al.
(Continued)

FOREIGN PATENT DOCUMENTS

| CN | 104364605 A | 2/2015 |
| WO | WO 02/13232 A2 | 2/2002 |
| WO | WO 2012/171687 A1 | 12/2012 |

OTHER PUBLICATIONS

International Search Report directed to Related International Patent Application No. PCT/EP2016/056254, dated Jul. 8, 2016; 6 pages.
(Continued)

*Primary Examiner* — Aklilu Woldemariam
(74) *Attorney, Agent, or Firm* — Sterne, Kessler, Goldstein & Fox P.L.L.C.

(57) ABSTRACT

A lithographic manufacturing system produces periodic structures with feature sizes less than 10 nm and a direction of periodicity (D). A beam of radiation (1904) having a range of wavelengths in the EUV spectrum (1-100 nm or 1-150 nm) is focused into a spot (S) of around 5 μm diameter. Reflected radiation (1908) is broken into a spectrum (1910) which is captured (1913) to obtain a target spectrum signal (ST). A reference spectrum is detected (1914) to obtain a reference spectrum signal (SR). Optionally a detector (1950) is provided to obtain a further spectrum signal (SF) using radiation diffracted at first order by the grating structure of the target. The angle of incidence (α) and azimuthal angle (φ) are adjustable. The signals (ST, SR, SF) obtained at one or more angles are used to calculate measured properties of the target, for example CD and overlay.

22 Claims, 17 Drawing Sheets

(51) Int. Cl.
G01N 21/88 (2006.01)
G03F 7/20 (2006.01)

(52) U.S. Cl.
CPC .............. *G03F 7/70625* (2013.01); *G01N 2021/95676* (2013.01); *G06K 9/00* (2013.01)

(58) Field of Classification Search
CPC .......... G03F 7/70433; G03F 1/44; G03F 1/84; G03F 7/70091; G03F 7/70125; G03F 7/70425; G03F 7/705; G03F 7/70616; G03F 7/70141; G03F 9/7046; G03F 9/7076; G03F 7/70191; G03F 7/70633; G03F 9/7049; G03F 7/70683; G03F 7/70158; G03F 7/70591; G03F 7/70641; G03F 9/7026; G03F 9/7065; G01J 3/4412; G01J 3/2803; G01J 3/44; G01J 3/18; G01N 21/4788; G01N 21/9501; G01N 21/956; G01N 21/47; G01N 2021/95676; G01N 21/95607; G01B 11/02; G01B 11/22; G01B 11/14; G02B 27/58; G02B 21/0016; G02B 21/06; G02B 21/361; G02B 21/364; G02B 21/365; G06T 7/001; H01L 21/67282; H01L 21/681; G06F 17/50
USPC ....... 382/106, 144; 355/44, 67, 77; 250/206, 250/580
See application file for complete search history.

(56) References Cited

U.S. PATENT DOCUMENTS

| 9,863,761 | B2 | 1/2018 | Shi et al. |
| 2004/0012775 | A1* | 1/2004 | Kinney ............... G01N 21/9501 356/237.2 |
| 2004/0075830 | A1 | 4/2004 | Miyake et al. |
| 2005/0219548 | A1* | 10/2005 | Muroya ................. G01B 11/24 356/504 |
| 2006/0066855 | A1* | 3/2006 | Boef ................... G03F 7/70341 356/401 |
| 2007/0146708 | A1 | 6/2007 | Hagiwara |
| 2007/0182964 | A1 | 8/2007 | Den Boef et al. |
| 2007/0224518 | A1 | 9/2007 | Yokhin et al. |
| 2008/0239265 | A1 | 10/2008 | Den Boef |
| 2008/0273662 | A1 | 11/2008 | Yun et al. |
| 2008/0279442 | A1* | 11/2008 | Den Boef ................. G03F 1/84 382/144 |
| 2010/0103433 | A1 | 4/2010 | Ausschnitt |
| 2010/0265506 | A1* | 10/2010 | Den Boef ........... G03F 7/70633 356/399 |
| 2011/0027704 | A1* | 2/2011 | Cramer ............... G03F 7/70641 430/30 |
| 2011/0102753 | A1* | 5/2011 | Van De Kerkhof ........................ G01N 21/4788 355/27 |
| 2011/0137625 | A1* | 6/2011 | Dirks ...................... G03F 7/705 703/2 |
| 2012/0044470 | A1* | 2/2012 | Smilde ...................... G03F 1/44 355/53 |
| 2012/0075456 | A1 | 3/2012 | Seitz |
| 2012/0123748 | A1* | 5/2012 | Aben .................. G03F 7/70483 703/2 |
| 2012/0162755 | A1 | 6/2012 | Stroessner et al. |
| 2012/0212749 | A1* | 8/2012 | Den Boef ........... G02B 21/0048 356/615 |
| 2012/0236994 | A1 | 9/2012 | Hieke |
| 2012/0330592 | A1* | 12/2012 | Bottiglieri ............ G01N 21/956 702/85 |
| 2013/0035911 | A1* | 2/2013 | Pisarenco ............... G03F 7/705 703/2 |
| 2013/0066597 | A1* | 3/2013 | Van Beurden ..... G01N 21/4788 703/1 |
| 2013/0073070 | A1* | 3/2013 | Tsai ....................... G01N 21/47 700/103 |
| 2013/0144560 | A1* | 6/2013 | Pisarenco ............. G01N 21/47 702/189 |
| 2013/0162996 | A1* | 6/2013 | Straaijer ............. G03F 7/70633 356/369 |
| 2013/0215404 | A1 | 8/2013 | Den Boef |
| 2013/0271740 | A1* | 10/2013 | Quintanilha ............ G03F 1/144 355/67 |
| 2013/0308125 | A1 | 11/2013 | Perlitz |
| 2013/0321609 | A1 | 12/2013 | Seitz et al. |
| 2014/0211185 | A1* | 7/2014 | Cramer ..................... G01J 3/18 355/67 |
| 2015/0109624 | A1* | 4/2015 | Kreuzer ................ G03F 9/7069 356/508 |
| 2015/0176979 | A1* | 6/2015 | Mathijssen ......... G03F 7/70633 355/77 |
| 2015/0308895 | A1 | 10/2015 | Den Boef |
| 2015/0308966 | A1* | 10/2015 | Grootjans ........ G01N 21/95607 355/67 |
| 2015/0331336 | A1 | 11/2015 | Quintanilha et al. |
| 2015/0346605 | A1 | 12/2015 | Den Boef et al. |
| 2015/0355554 | A1* | 12/2015 | Mathijssen ........... G03F 9/7046 355/67 |
| 2016/0223916 | A1* | 8/2016 | Van Beurden .......... G03F 7/705 |

OTHER PUBLICATIONS

Written Opinion of the International Searching Authority directed to related Patent Application No. PCT/EP2016/056254, dated Jul. 8, 2016; 6 pages.

Scholze, F. et al. "The influence of line edge roughness and CD uniformity on EUV scatterometry for CD characterization of EUV masks" Proc. Of SPIE vol. 6617, 66171A (2007).

M. A. Henn et al. "Improved reconstruction of critical dimensions in extreme ultraviolet scatterometry by modeling systematic errors", Meas. Sci. Technol., 25(2014); 9 pages.

J. Wernecke et al. "Direct structural characterisation of line gratings with grazing incidence small-angle x-ray scattering", Review of Sci. Instruments, 83 (2012); pp. 103906-1-103906-8; 8 pages.

Danylyuk, S. et al., "Multi-angle spectroscopic EUV reflectometry for analysis of thin films and interfaces", Phys. Status Solidi C 12, No. 3, 2015; pp. 318-322.

Farahzadi, A., et al., "The task of EUV-reflectometry for HVM of EUV-masks: first steps", EMLC 2009, Jan. 12-15, 2009; 7 pages.

Kato, A., et al., "The effect of line roughness on the reconstruction of line profiles for EUV masks from EUV scatterometry", Proceedings of the SPIE—The International Society for Optical Engineering, 2010, vol. 7636; pp. 763621-1-763621-8.

LeMaillet, P., et al., "Intercomparison between optical and x-ray scatterometry measurements of FinFET structures", Proc. of SPIE, 2013, vol. 8681, 86810Q; 8 pages.

Lerbert, R. et al., "AIXUV's Tools for EUV-Reflectometry", downloaded Jan. 23, 2015 from http://sematech.org/meetings/archives/litho/7870/proceedings/posters/Metrology_ME/07-ME-78%20Wies_AIXUV.pdf; 9 pages.

Scholze, F. et al., "Characterization of nano-structured surfaces by EUV scat-terometry", Journal of Physics: Conference Series 311 (2011), 13th International Conference on Metrology and Properties of Engineering Surfaces; 7 pages.

Tetsuo, H. et al., "Imaging of extreme-ultraviolet mask patterns using coherent extreme-ultraviolet scatterometry microseope based on, coherent diffraction imaging", Journal of Vacuum Science and Technology, B 29(6), Nov./Dec. 2011; pp. 06F503-1-06F503-7.

Törmä P. et al., "Performance and Properties of Ultra-Thin Silicon Nitride X-ray Windows", IEEE Transactions on Nuclear Science, vol. 61, No. 1, Feb. 2014; pp. 695-699.

Chinese Office Action with English-language Translation Attached from Related Chinese Patent Application No. 2016800172043, dated Jun. 1, 2018; 21 pages.

* cited by examiner

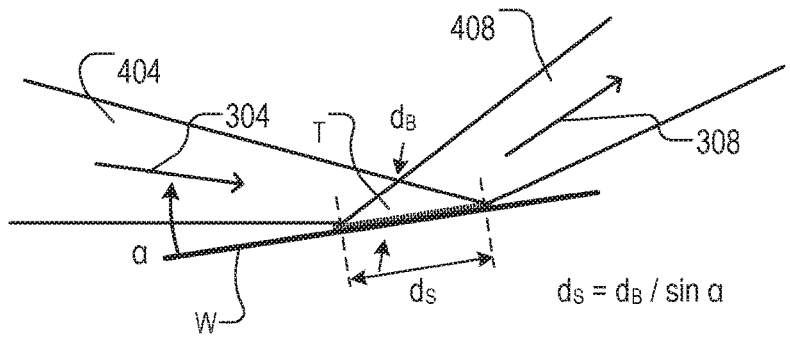
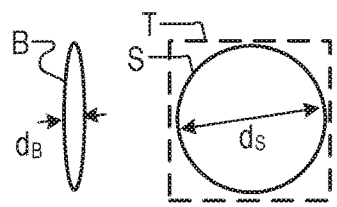 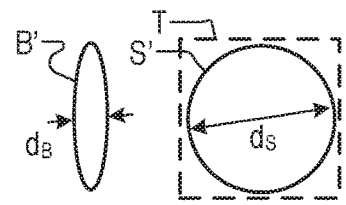
Fig. 4(b)   Fig. 4(c)
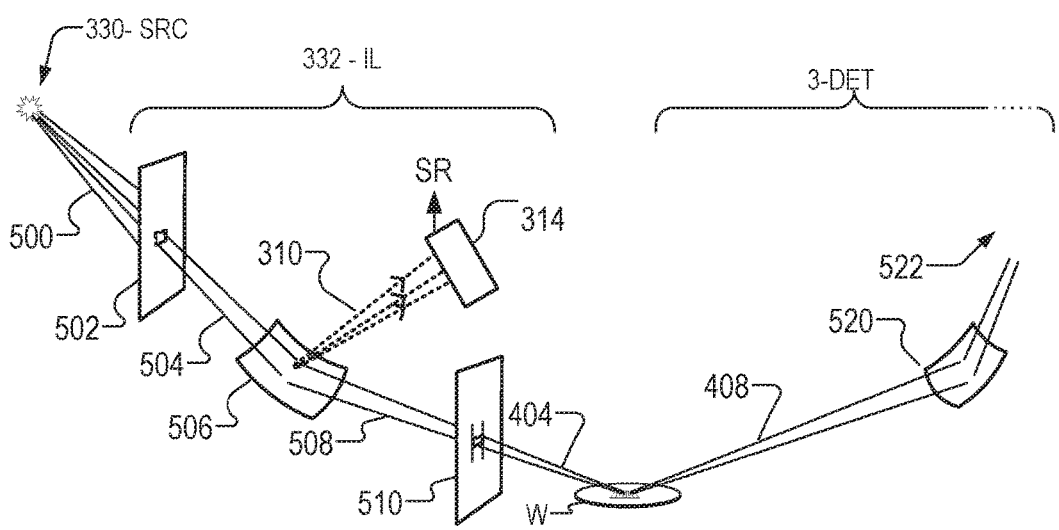
Fig. 5

METROLOGY METHODS, METROLOGY APPARATUS AND DEVICE MANUFACTURING METHOD

CROSS REFERENCE TO RELATED APPLICATIONS

This application claims benefit to EP Application 15160786.8, which is incorporated by reference herein in its entirety.

BACKGROUND

Field of the Invention

The present invention relates to methods and apparatus for metrology usable, for example, in the manufacture of devices by lithographic techniques and to methods of manufacturing devices using lithographic techniques. Methods of measuring critical dimension (line width) are described, as a particular application of such metrology. Methods of measuring asymmetry-related parameters such as overlay are also described.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer).

In lithographic processes, it is desirable frequently to make measurements of the structures created, e.g., for process control and verification. Various tools for making such measurements are known, including scanning electron microscopes (SEM), which are often used to measure critical dimension (CD). Other specialized tools are used to measure parameters related to asymmetry. One of these parameters is overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis. Compared with SEM techniques, optical scatterometers can be used with much higher throughput, on a large proportion or even all of the product units.

The targets used by conventional scatterometers are relatively large, e.g., 40 µm by 40 µm, gratings and the measurement beam generates a spot that is smaller than the grating (i.e., the grating is underfilled). In order to reduce the size of the targets, e.g., to 10 µm by 10 µm or less, e.g., so they can be positioned in amongst product features, rather than in the scribe lane, so-called "small target" metrology has been proposed, in which the grating is made smaller than the measurement spot (i.e., the grating is overfilled). These targets can be smaller than the illumination spot and may be surrounded by product structures on a wafer. Typically small targets are used for measurement of overlay and other performance parameters that can be derived from measurements of asymmetry in the grating structure. By placing the target in among the product features ("in-die target"), it is hoped to increase accuracy of measurement. The improved accuracy is expected for example because the in-die target is affected by process variations in a more similar way to the product features, and less interpolation may be needed to determine the effect of a process variation at the actual feature site. These optical measurements of overlay targets have been very successful in improving overlay performance in mass production.

As technology develops, however, performance specifications become ever tighter. Moreover, small target techniques have not been developed for measurement of other parameters such as line width or critical dimension (CD). A further limitation of current methods is that they are made with optical wavelengths, much greater than the typical dimensions of real product features. A particular parameter of interest is linewidth (CD), and a suitable small-target method for CD measurement has not yet been devised.

As an alternative to optical metrology methods, it has also been considered to use X-rays to measure overlay in a semiconductor device. One technique is known as transmissive small angle X-ray scattering or T-SAXS. A T-SAXS apparatus applied to measurement of overlay is disclosed in US 2007224518A (Yokhin et al, Jordan Valley), and the contents of that application are incorporated herein by reference. Profile (CD) measurements using T-SAXS are discussed by Lemaillet et al in "Intercomparison between optical and X-ray scatterometry measurements of FinFET structures", Proc. of SPIE, 2013, 8681. T-SAXS uses X-rays of wavelength less than 1 nm, and so targets for T-SAXS can be made of product-like features. Unfortunately, T-SAXS signals tend to be very weak, especially when the target size is small. Therefore the measurements tend to be too time-consuming for use in high-volume manufacturing. T-SAXS apparatus can be used to measure targets small enough to be considered for placement among the product features. Unfortunately, the small target size requires a small spot size and consequently even longer measurement times.

Reflectometry techniques using X-rays (GI-XRS) and extreme ultraviolet (EUV) radiation at grazing incidence are known for measuring properties of films and stacks of layers on a substrate. Within the general field of reflectometry, goniometric and/or spectroscopic techniques can be applied. In goniometry, the variation of a reflected beam with different incidence angles is measured. Spectroscopic reflectometry, on the other hand, measures the spectrum of wavelengths reflected at a given angle (using broadband radiation). For example, EUV reflectometry has been used for inspection of mask blanks, prior to manufacture of reticles (patterning devices) for use in EUV lithography. Work on these techniques has been described for example by S Danylyuk et al in "Multi-angle spectroscopic EUV reflectometry for analysis of thin films and interfaces", Phys. Status Solidi C 12, 3, pp. 318-322 (2015). However, such measurements are different from the measurement of CD in a periodic structure. Moreover, particularly in view of the very shallow grazing incidence angles involved, none of these known techniques is suitable for metrology on small targets such as an in-die grating.

SUMMARY OF THE INVENTION

The invention aims to provide alternative methods of small target metrology, overcoming one or more of the drawbacks of the optical and X-ray methods described above. A particular desire is to measure parameters for example at locations within product areas on a semiconductor substrate, while improving the speed with which such measurements can be performed and while adapting to the smaller dimensions of features made by current and future lithographic technologies.

The invention in a first aspect provides a method of measuring a property of a structure manufactured by a lithographic process, the method comprising:

(a) irradiating a periodic structure with a beam of radiation along an irradiation direction, the periodic structure having been formed by said lithographic process on a substrate and having a periodicity in at least a first direction, the radiation comprising a plurality of wavelengths in the range of 1-100 nm, the irradiation direction being greater than 2° from a direction parallel to the substrate;

(b) detecting a spectrum of radiation reflected by the periodic structure, and (c) processing signals representing the detected spectrum to determine a property of the periodic structure.

The inventors have recognized that radiation in the extreme ultraviolet (EUV) waveband offers particular advantages for metrology of CD and other properties of small metrology targets having the form of periodic structures. Compared with the optical scatterometry commonly practiced, EUV rays will not be strongly influenced by underlying features, and modeling of the periodic structure itself can be more accurate as a result. Compared with X-rays, there is potential to focus the EUV radiation to a finer spot without undue loss of power. Compared with X-rays, there is potential to use a much higher angle of incidence. By providing in addition a suitable EUV optical system for illumination and detection of the target, EUV radiation can be formed into a small enough spot for in-die metrology, even when the spot is elongated by the grazing incidence. In order to obtain sufficient information for CD metrology, spectral properties across a range of EUV wavelengths can be measured.

Reference to a range of wavelengths from 1 nm to 100 nm, or to 1 nm to 150 nm, is not intended to mean that the apparatus or method should use wavelengths across that entire wave range, or even be capable of doing so. An individual implementation may choose to work with wavelengths over only a subset of the range. The appropriate range will depend on the availability of suitable sources, and the dimension of structures to be measured.

Optionally, the method is performed such that a direction of irradiation lies outside a plane defined by the first direction and a direction normal to the substrate so as to define a non-zero azimuthal angle relative to the first direction, when viewed from the substrate. The method disclosed herein may be performed using an azimuthal angle that has been determined to optimize the accuracy of measurement. The azimuthal angle may be for example greater than 15, 30, 45 degrees, even up to eighty degrees if desired. The non-zero azimuthal angle can be achieved by using what is referred to in other measurement techniques as a conical mount.

The inventor has recognized that, by using a conical mount in EUV reflectometry, for CD metrology, the azimuthal angle is selected so that a diffraction efficiency of the periodic structure in one or more non-zero diffraction orders is greater than would be the case for an irradiation direction of zero azimuthal angle. Depending on the target structure and materials, spectral signals in the zero and/or higher diffraction orders important for the measurement of its structure may be very weak at one azimuthal angle, but stronger at another.

In an embodiment, for example, the azimuthal angle may be selected so that a diffraction efficiency of the periodic structure in a first order of diffraction is more than two times, optionally more than five times or more than ten times the diffraction efficiency for zero azimuthal angle. Alternatively, or in addition, the azimuthal angle may be selected so that a diffraction efficiency of the periodic structure in a plurality of non-zero diffraction orders is greater than would be the case for an irradiation direction of zero azimuthal angle.

In one embodiment, the steps (a) and (b) are repeated using different polar angles and wherein in step (c) signals representing the scattered radiation detected using a plurality of different polar angles are used to determine the property of the periodic structure.

The invention further provides a metrology apparatus for use in measuring performance of a lithographic process, the apparatus comprising:

an irradiation system for generating a beam of radiation, the radiation comprising a plurality of wavelengths in the range of 1-100 nm;

a substrate support operable with the irradiation system for irradiating a periodic structure formed on the substrate with radiation along an irradiation direction, the irradiation direction being greater than 2° from a direction parallel to the substrate; and a detection system for detecting a spectrum of radiation reflected by the periodic structure.

In a particular implementation, the substrate support is adapted to receive semiconductor wafers (for example 300 mm wafers) from an automated wafer handler.

In a second aspect of the invention, there is provided method of measuring a property of a structure manufactured by a lithographic process, the method comprising:

(a) irradiating a periodic structure with a beam of radiation along an irradiation direction, the periodic structure having been formed by said lithographic process on a substrate and having a periodicity in at least a first direction, the radiation comprising a plurality of wavelengths in the range of 1-100 nm, the irradiation direction being greater than 2° from a direction parallel to the substrate;

(b) detecting a spectrum of radiation diffracted by the periodic structure, the non-zero diffraction order being spread into said spectrum by the periodic structure reflected by the periodic structure; and, (c) processing signals representing the detected spectrum to determine a property of the periodic structure.

In yet another aspect, the invention provides a device manufacturing method comprising:

transferring a pattern from a patterning device onto a substrate using a lithographic process, the pattern defining at least one periodic structure;

measuring one or more properties of the periodic structure to determine a value for one or more parameters of the lithographic process; and applying a correction in subsequent operations of the lithographic process in accordance with the measured property, wherein the step of measuring the properties of the periodic structure includes measuring a property by a method according to the first or second aspect of the invention, set forth above.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example, with reference to the accompanying drawings in which:

FIG. 4 (a) illustrates by a schematic side view the elongation of a spot of radiation under grazing incidence, with schematic representations of beam cross-section B an spot S shown schematically at (b) and (c) for different angles of incidence;

FIG. 5 illustrates schematically the components of an illumination system in one embodiment of the apparatus of FIG. 3;

FIG. 8 (d) to (f) comprises graphs of calculated reflectivity over the EUV spectrum, for different angles of incidence, in the case of (d) a grating structure with a first side wall angle (e) a grating structure with a second side wall angle, with differences between these reflectivities (d) and (e) being shown at (f);

DETAILED DESCRIPTION OF EXEMPLARY EMBODIMENTS

Before describing embodiments of the invention in detail, it is instructive to present an example environment in which embodiments of the present invention may be implemented.

Figure 1:
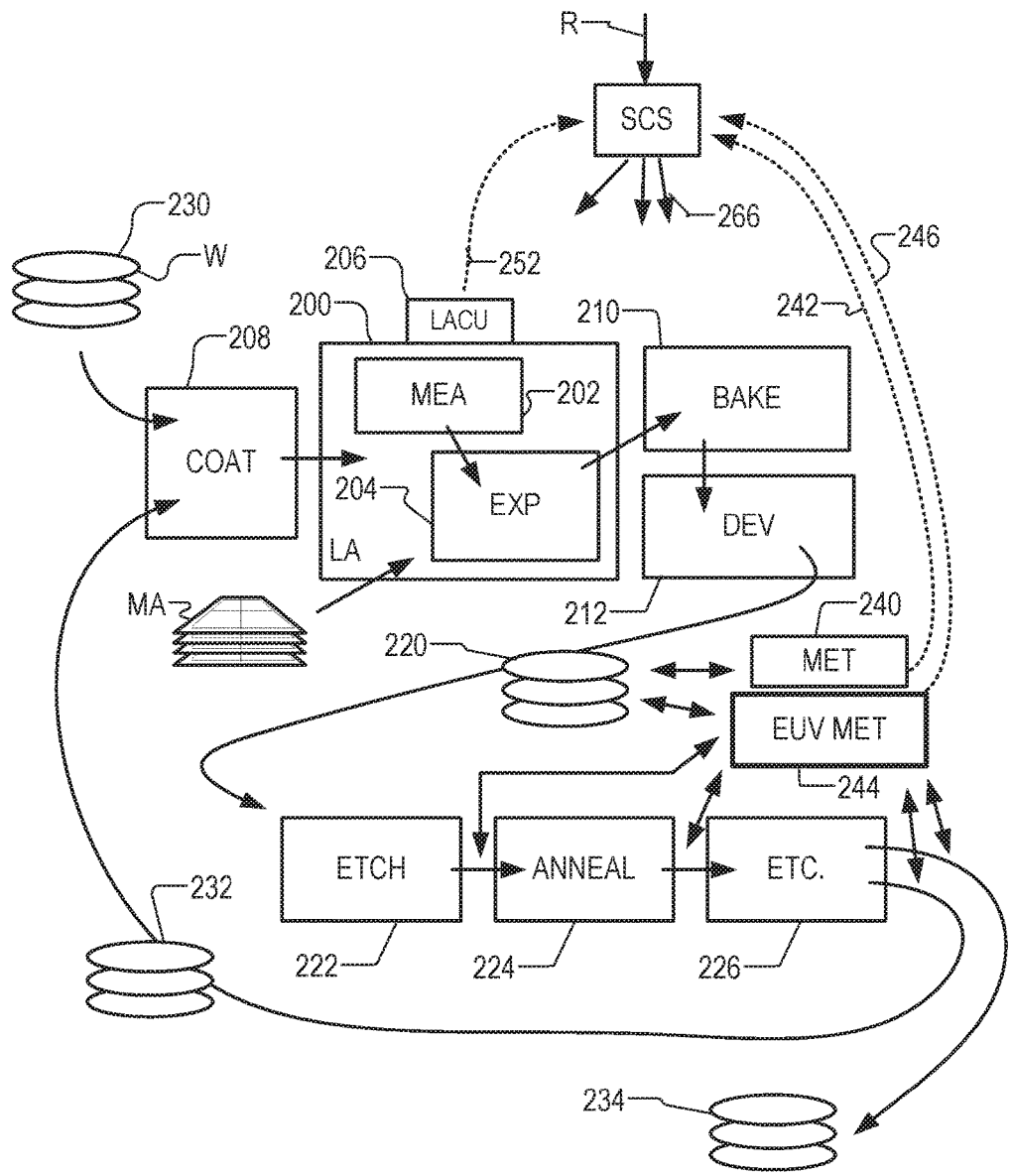
FIG. 1 depicts a lithographic apparatus together with other apparatuses forming a production facility for semiconductor devices.

FIG. 1 at 200 shows a lithographic apparatus LA as part of an industrial facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables WTa and WTb and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system MET which receives some or all of the substrates W that have been processed in the litho cell. Metrology results are provided directly or indirectly to the supervisory control system SCS. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 240 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

Each generation of lithographic manufacturing technology (commonly referred to as a technology "node") has tighter specifications for performance parameters such as CD. One of the main challenges in metrology is that the metrology target size is desired to be smaller than the targets customarily used with metrology apparatus 240. For example, a present goal is to use targets with a size of 5 µm×5 µm or smaller. These small sizes would permit wider use of so-called "in-die" or "on product" metrology, where targets are located among the product features (instead of being confined in scribe lane areas between product areas). The only metrology technique currently used for in-die CD metrology is electron microscopy (CD-SEM). This known technique shows limitations for future nodes, and only provides very limited geometrical information of the structure.

In the present disclosure, it is proposed to use EUV reflectometry, in particular spectroscopic EUV reflectometry, as a CD-metrology method solution for future technological nodes. It will be demonstrated that EUV reflectometry offers benefits of high sensitivity, being robust against process variations and being selective for a parameter of interest. For this purpose, the manufacturing system illustrated in FIG. 1 includes one or more EUV metrology apparatuses 244 in addition to the optical scatterometer 240. This EUV metrology apparatus provides additional metrology results 246 which can be used by supervisory control system SCS to achieve further control of quality and improvement in performance of the lithographic manufacturing system as a whole. Like the optical scatterometer 240, EUV can be used to measure structures within the resist material treated within the litho cell (After Develop Inspection or ADI), and/or to measure structures after they have been formed in harder material (After Etch Inspection or AEI). For example, substrates may be inspected using EUV metrology apparatus 244 after they have been processed by the developing apparatus 212, etching apparatus 222, annealing apparatus 224 and/or other apparatus 226. By contrast, X-ray techniques will generally be limited to AEI and cannot be used to measure structures formed only in the resist. This restricts the possibility to re-work substrates if they fail an inspection. The limited power of compact x-ray sources means that known T-SAXS techniques suffer from a very low throughput, especially for small size metrology targets.

EUV Spectroscopic Reflectometry

Figure 2:
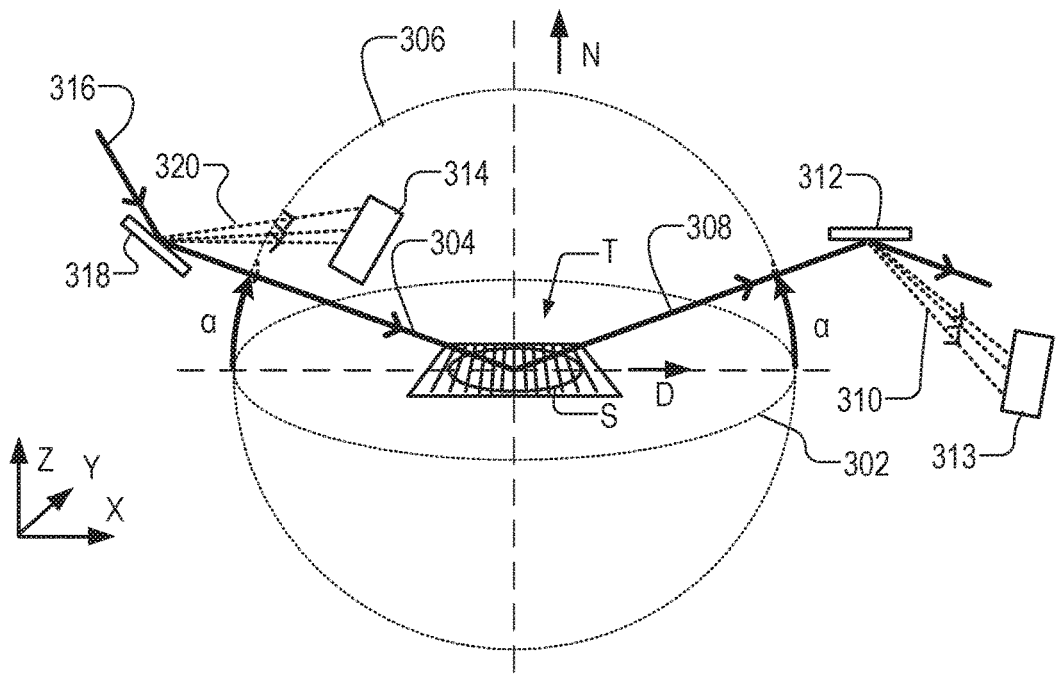
FIG. 2 illustrates the geometry of incident and reflected rays in relation to a grating target in a metrology method according to a first embodiment of the present invention.
Figure 3:
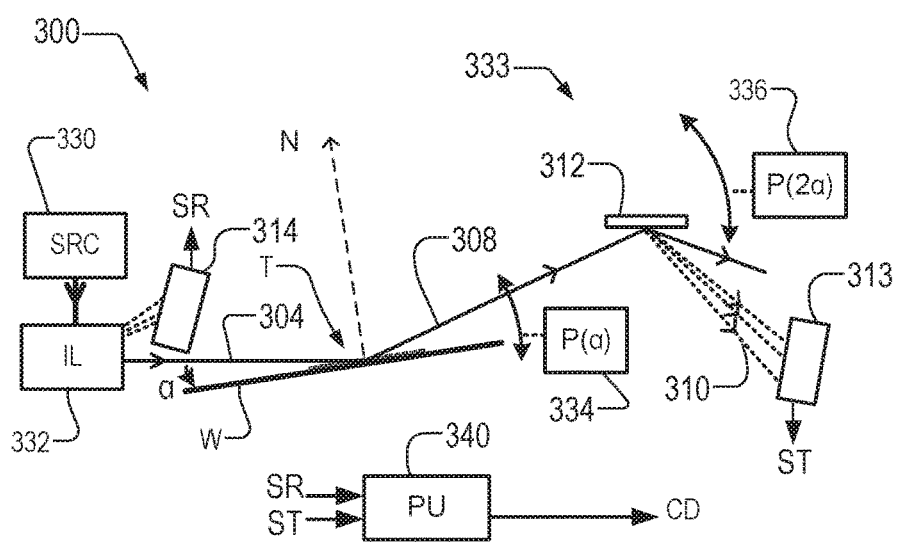
FIG. 3 illustrates schematically the components of a metrology apparatus, performing the method of FIG. 2.
Figure 6A:
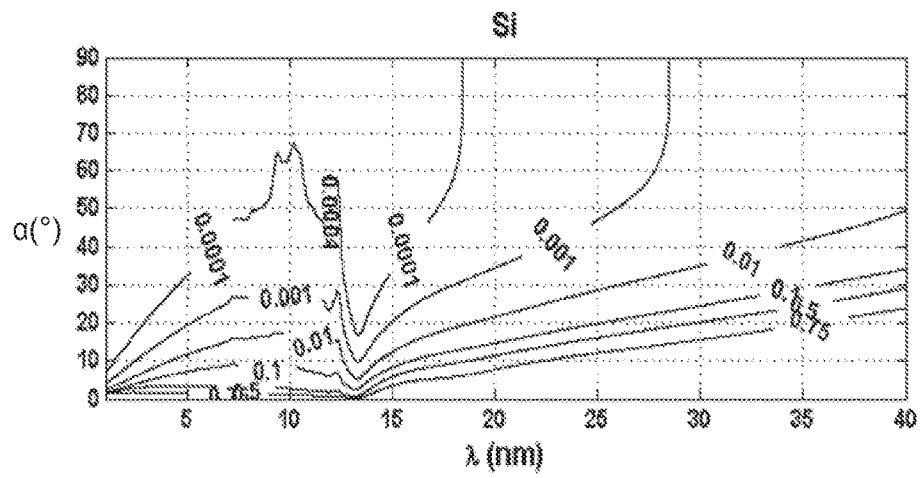
FIG. 6 illustrates variations of reflectivity for different materials and different angles of grazing incidence, over a range of wavelengths within part of the EUV spectrum.
Figure 6B:
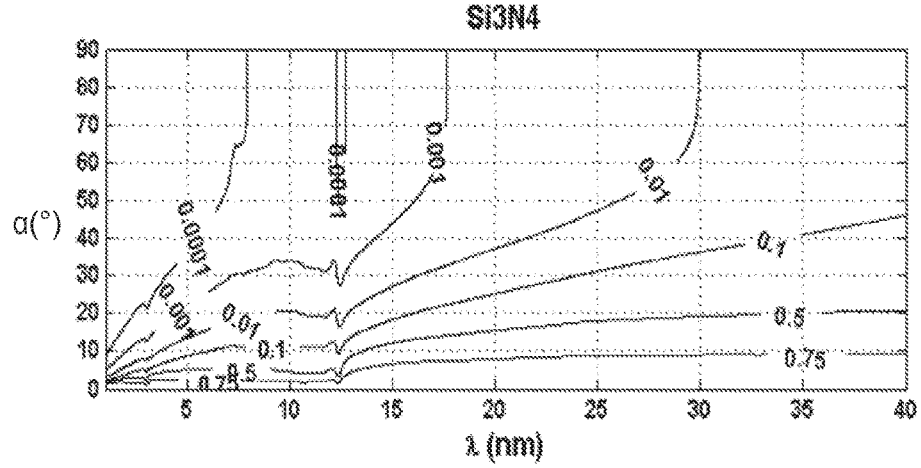
Figure 6C:
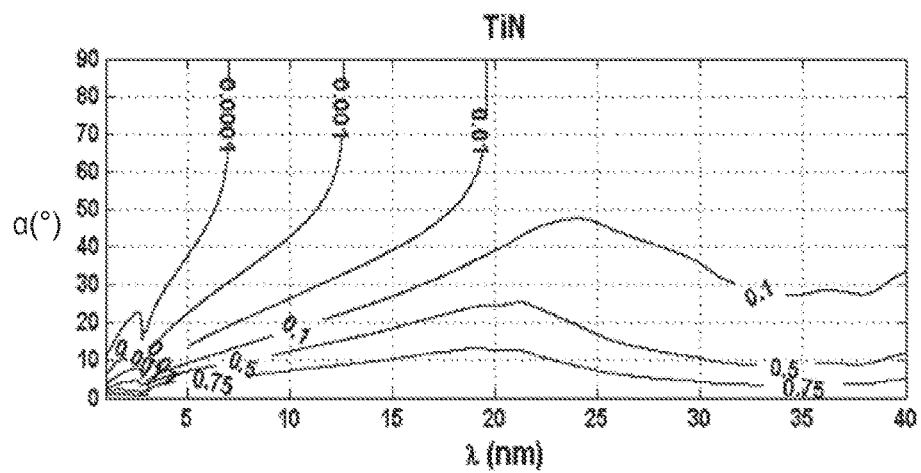
Figure 6D:
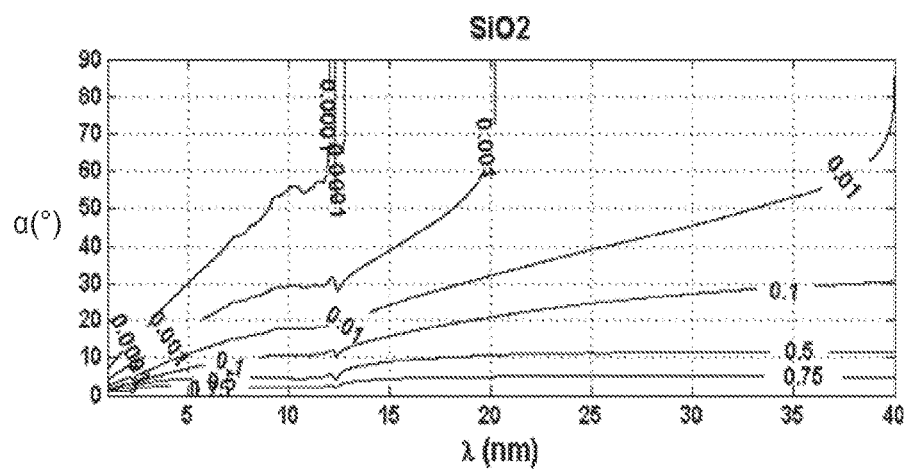
Figure 6E:
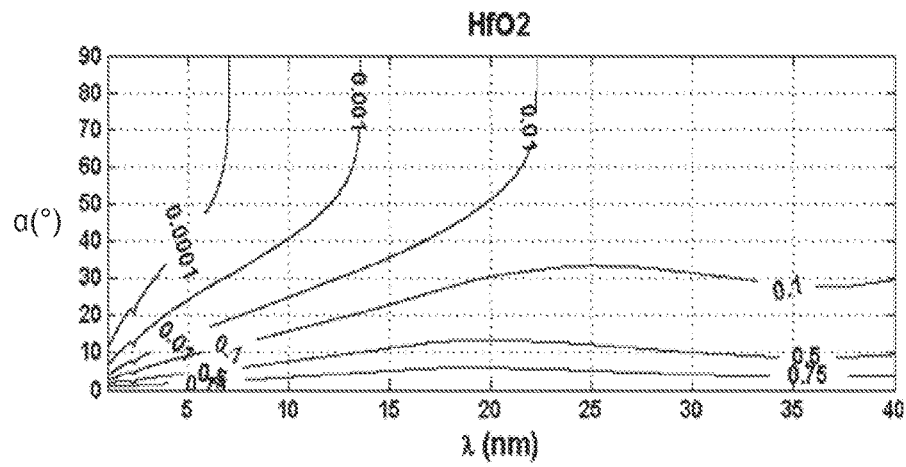
Figure 6F:
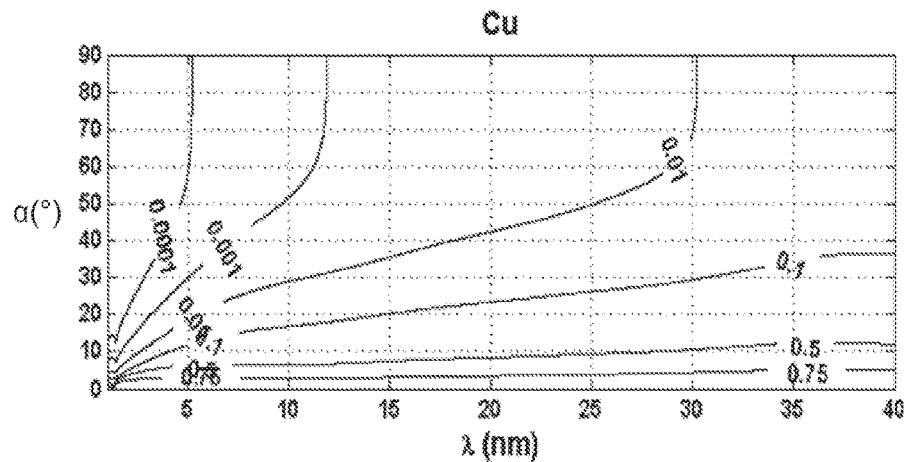

FIG. 2 illustrates an EUV metrology method while FIG. 3 illustrates an EUV metrology apparatus 300. The apparatus can be used as an example of EUV metrology apparatus 244 for measuring parameters of substrates W processed in the manufacturing system of FIG. 1.

In FIG. 2, the target T is represented schematically as comprising a one-dimensional grating structure at the origin of a spherical reference frame. Axes X, Y and Z are defined relative to the target. (Of course any arbitrary coordinate system can be defined in principle, and each component may have its own local reference frame, that can be defined relative to the one shown.) The direction of periodicity D of the target structure is aligned with the X axis. The drawing is not a true perspective drawing, but a schematic illustration only. The X-Y plane is the plane of the target and substrate, and for clarity is shown tilted toward the viewer, represented by an oblique view of circle 302. The Z direction defines the direction N normal to the substrate. In FIG. 2, one of the incident rays is labeled 304 and has an angle α of grazing incidence. In this example, the incident ray 304 (and all incident rays forming the radiation spot S) lie substantially in a plane parallel to the X-Z plane, that is a plane defined the directions D and N and represented by circle 306. A reflected ray 308 that is not scattered by the periodic structure of the target T emerges towards the right hand side of the target in the diagram, with an elevation angle α.

To perform spectroscopic reflectometry, ray 308 and other reflected rays are broken into a spectrum 310, comprising rays of different wavelengths. The spectrum may be produced for example using a grazing incidence diffraction grating 312. The spectrum is detected by a detector 313. This detector, which may for example be a CCD image detector having an array of pixels, is used to transform the spectrum into electrical signals and eventually digital data for analysis.

In a practical system, the spectrum of radiation 304 may be subject to time variations, which would disturb the analysis. In order to normalize the detected spectrum against these variations, a reference spectrum is captured by a second detector 314. To produce the reference spectrum, source radiation 316 is diffracted by another diffraction grating 318. A zero order reflected ray of grating 318 forms the incident ray 304, while the first order diffracted rays 320 of grating 318 form the reference spectrum detected by reference spectrum detector 314. Electrical signals and data representing the reference spectrum are obtained for use in the analysis.

From the measured spectrum, obtained for one or more values of incidence angle α, a measurement of a property of the target structure T can be calculated in a manner described further below.

Turning to FIG. 3, EUV metrology apparatus 300 is provided for measuring properties of a metrology target T formed on substrate W, by the method of FIG. 2. Various hardware components are represented schematically. The practical implementation of these components can be performed by the relevant skilled persons applying a mixture of existing components and specially-designed components, according to well-known design principles. A support (not shown in detail) is provided for holding the substrate at a desired position and orientation relative to other components to be described. A radiation source 330 provides radiation to an illumination system 332. Illumination system 332 provides a beam of EUV radiation represented by ray 304 which forms a focused irradiation spot on target T. Illumination system 332 also provides the reference spectrum 320 to detector 314. Components 312, 313 etc. may be conveniently considered as a detection system 333.

Substrate W in this example is mounted on a movable support having a positioning system 334 such that an angle of incidence α of ray 304 can be adjusted. In this example, it is chosen as a matter of convenience to tilt the substrate W to change the incidence angle, while the source 330 and illumination system 332 remain stationary. In order to catch the reflected ray 308, detection system 333 is provided with a further movable support 336, so that it moves through an angle 2α relative to the stationary illumination system, or through an angle α relative to the substrate. In the grazing incidence regime of reflectometry, it is convenient to define the incidence angle α by reference to the plane of the substrate, as shown. Of course, it could equally be defined as an angle between the direction of incidence of incident ray I and a direction N normal to the substrate.

Additional actuators, not shown, are provided for bringing each target T into a position where the focused spot S of radiation is located. (Looking at it another way, to bring the spot to the position where the target is located.) In a practical application, there may be a succession of individual targets or target locations to be measured on a single substrate, and a succession of substrates too. It is immaterial, in principle, whether the substrate and target are moved and reoriented while the illumination system and detector stay still, or whether the substrate stays still while the illumination system and detector are moved, or whether different components of the relative movement are achieved by a combination of these techniques. The present disclosure encompasses all these variants.

As already described with reference to FIG. 2, the radiation reflected by target T and substrate W is split into a spectrum 310 of rays of different wavelengths, before it impinges on detector 313. Detector 306 comprises for example a position-sensitive EUV detector, typically an array of detector elements. The array may be a linear array, but in practice a 2-dimensional array of elements (pixels) may be provided. Detector 313 may be for example a CCD (charge coupled device) image sensor.

A processor 340 receives signals from the detectors 313 and 314. In particular, signal ST from detector 313 represents the target spectrum and signal SR from detector 314 represents the reference spectrum. Processor 340 can subtract the reference spectrum from the target spectrum to contain a reflection spectrum of the target, normalized against variation in the source spectrum. The resulting reflection spectra for one or more angles of incidence are used in the processor to calculate a measurement of property of the target, for example CD or overlay.

In practice, radiation from source 330 may be provided in a series of short pulses and signals SR and ST may be captured together for each pulse. Difference signals for each individual pulse are calculated, before being aggregated into an overall reflection spectrum for this target at this angle of incidence. In this way, instability of the source spectrum between pulses is corrected for. The pulse rate may be thousands, or even tens of thousands per second (hertz). The number of pulses aggregated to measure one reflection spectrum may be tens or hundreds, for example. Even with so many pulses, the physical measurement takes a fraction of one second.

In the application of this EUV-SR to metrology in semiconductor manufacturing, small grating targets can be used. Multiple diffraction spectra are captured using detectors 313 and 314, while setting the grazing angle of incidence α to various different values. Using the detected spectra and a mathematical model of the target structure, reconstruction calculations can be performed to arrive at measurement of CD and/or other parameters of interest. An example reconstruction method will be illustrated further below.

Considering briefly the target itself, dimensions of the lines and spaces will depend on the target design, but the period of the structure may be for example less than 100 nm, less than 50 nm, less than 20 nm, even less than 10 nm and down to 5 nm. The lines of the grating structure may be of the same dimension and pitch as product features in a product area of the substrate. The lines of the grating structure may in fact be the lines of a product structure, rather than a target structure formed, within a dedicated target area, solely for the purposes of metrology. Such small features may be formed for example in an EUV lithography process, by imprint lithography or by direct-write methods. Such small features may also be formed using present-day DUV lithography, by a so-called double-patterning processes (generally multiple-patterning). Techniques in this category include pitch-doubling, for example by litho-etch-litho-etch (LELE) and self-aligned dual-damascene in back end-of the line (BEOL) layers. For the purposes of explanation, it will be assumed in the following examples that CD is the parameter of interest. However, where there are two gratings formed on top of one another, another parameter of interest maybe overlay. This can be measured based on asymmetry in the EUV-SR diffraction orders, as described separately below. The incidence angle can be elevated if necessary to achieve adequate penetration to the lower structure.

In the multiple-patterning process, structures are formed in one layer of the product not in one patterning operation but in two or more patterning steps. Thus, for example, a first population of structures may be interleaved with a second population of structures, and the populations are formed in different steps, so as to achieve a higher resolution than one step alone can produce. While the placement of the populations should be identical and perfect in relation to other features on the substrate, of course every real pattern exhibits a certain positional offset. Any unintentional positional offset between the populations can be regarded as a form of overlay, and can be measured by analogous techniques to those used to measure overlay between layers. Additionally, overlay against features in an underlying or overlying layer can be different for each population when multiple populations of features are formed in a single layer, and overlay for each of these populations can be measured separately if desired.

FIG. 4 illustrates the problem of elongation of a radiation spot, which is challenging for implementation of in-die metrology using grazing incidence reflectometry. In FIG. 4(a), the substrate W and target T are shown in cross-section.

Representative incident ray 304 and reflected ray 308 are illustrated, with incidence angle α relative to substrate W. As these are representative rays, it should be considered that the incident radiation as a whole comprises many rays, which form a beam indicated schematically at 404. Similarly, the reflected radiation comprises many rays 308 which form a beam indicated schematically at 408. In order to make use of the smallest possible target, a radiation spot is formed by focusing the rays of the beam 404, so that they converge to define a minimum beam diameter precisely where they meet the surface of substrate W. In the illustration, the incident beam 404 is convergent to a focus with a minimum diameter $d_B$. The reflected beam 408 (ignoring scattering effects) comprises divergent rays, as shown. Because grazing incidence angle α is relatively small (in other words, nearer to zero than to 90°) the diameter $d_S$ of the radiation beam 404, as projected on to the target T, is several times greater than the beam diameter $d_B$. The ratio between diameters $d_S$ and $d_B$ depends on the sine of angle α as shown in FIG. 4(a).

As shown in FIG. 4(b), to achieve circular spot S that fits within the area of target T, the beam 404 should have the strongly elliptical cross section shown at B. When the angle α is 5°, for example, the minimum diameter $d_B$ of the beam should be more than ten times smaller than the allowable diameter of the spot $d_S$ (sin 5°=0.087). For lower angles of incidence, the minimum diameter of the beam would have to be tens, hundreds or even thousands of times smaller. To obtain a spot that fits within a small target area such as 5 μm square would be impossible in practice. Even at α=5°, the minimum beam diameter $d_B$ should be around 436 nm to achieve a spot size under 5 μm. Conversely, as seen in FIG. 4(c), an increase in the grazing incidence angle α greatly relaxes the minimum diameter requirement of the beam 404. The ellipse B' can be much broader than the ellipse B, in order to achieve a spot S' that fits within the area of target T. For example, for α=20°, the beam diameter will be increased only by a factor of three. The minimum diameter $d_B$ can be as large as 1.7 μm without exceeding the 5 μm spot size. Compared with known techniques, particularly X-ray reflectometry (GI-XRS), the inventors have recognized that use of these higher incidence angles can bring smaller spot sizes within the capability of EUV optical design.

FIG. 5 illustrates one possible arrangement of the illumination system 332 in the apparatus of FIG. 3. A radiation source such as a plasma is represented at 330. For EUV lithography several types of sources have been tested and built experimentally or commercially. Any of these can be applied in the present apparatus, according to the range of wavelengths desired. Plasma sources include tin (Sn) but also Xe or Ar or Kr or Ne or N, or any combination of them. Laser driven light sources and harmonic generator sources can be applied. Plasma sources are not the only types of sources that can be applied, although at present they are the type that is most available in compact form. Synchrotron sources may yield more useful power levels, and be more controllable in wavelength and power, but these are not yet commercially available in a compact form.

A beam 500 of EUV radiation having desired spectral characteristics is emitted in a range of directions. At the exit of the source 330 (the entrance to the illumination system 332), a first aperture 502 is provided to serve as an entrance pupil for the illumination system. An incoming beam 504 with well-defined divergence impinges on a focusing optical element or system. This focusing system is implemented in the present illustration by a 2-dimensionally curved mirror 506, for example an ellipsoidal mirror. Mirror 506 produces a convergent beam 508, which is focused to form the spot at the target location on substrate W. Optionally, a second aperture 510 is provided to restrict the diameter of beam 404 at the target. In particular, aperture 510 may be made adjustable in height and/or width so that different shapes of beam B' can be generated according to different desires/sizes, and different incidence angles α.

Reflected beam 408 enters detection system 333 (not shown in this view), carrying information about the structure of the target. Optionally, a second focusing mirror 520 is provided to reduce divergence of the beam, as it enters detection system 333.

As seen in FIGS. 2 and 3, a reference spectrum 320 is formed and detected by reference spectrum detector 314. In the example illumination system illustrated in FIG. 5, the grating 318 for generating reference spectrum 320 is integrated in the curved mirror 506. In alternative embodiments, the reference spectrum grating could be provided as a separate element in series with the mirror 506. Further, in order to focus radiation from beam 504 into beam 508, the single two-dimensionally curved mirror 506 could be replaced by a series of two or more one-dimensionally curved (cylindrical) mirrors. The grating, wherever it is provided, may be of the "flat field" type, so that a well-resolved spectrum is formed across a linear or planar pixel array in detector 314. Similarly, where a two-dimensionally curved focusing mirror 520 is provided at a detection side, one or more dimensionally curved mirrors may be provided. The curved mirror can be integrated with the grating 312 which forms the spectrum 310 of the radiation reflected by the target. Note that it may not be necessary to focus the beam 408 in two dimensions in order to obtain a desired spectral resolution.

FIG. 6 shows contour plots (isoreflectance) of reflectance as a function of radiation wavelength λ and incidence angle α. Compared with, for example, X-rays, these simulations show that, for a variety of materials likely to be encountered in semiconductor manufacturing, the majority of radiation and the majority of wavelengths will be reflected even at relatively large values of the grazing incidence angle α higher than a few degrees. The contours are arrayed on a logarithmic scale. In every material, the strongest reflectance R (close to unity) is obtained for the lowest angles. The contour labeled $R=10^{-1}$ for example shows the incidence angle where one tenth of the incident radiation intensity is reflected, for a given wavelength.

Particularly in the range 15-40 nm (and above 40 nm, not shown), it will be seen that the reflectance of several of the materials of interest remains substantial even up to angles of 10, 20 and 30 degrees. Referring again to FIGS. 4 and 5, this range of incidence angles allows an optical design to be implemented which achieves the desired small radiation spot, even at grazing incidence using available EUV optical technology.

Figure 7A:
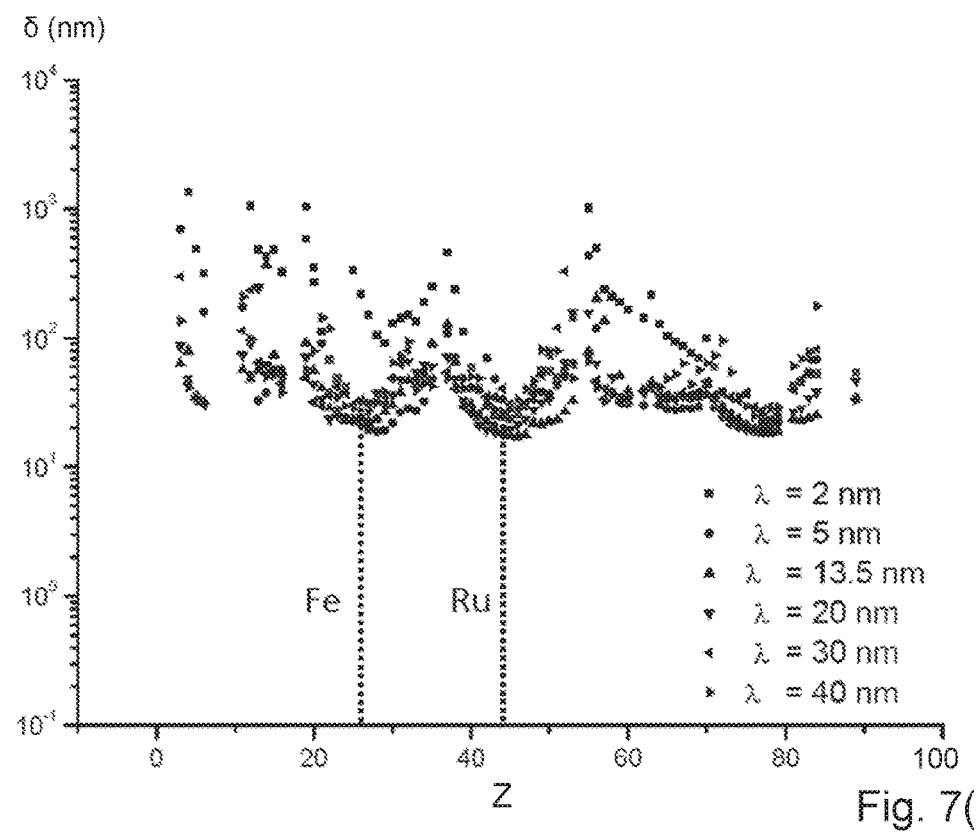
FIG. 7 illustrates (a) variation of penetration depth for EUV radiation in different materials, for a range of wavelengths at grazing incidence and (b) variation of penetration depth with incidence angle in silicon material, for a range of wavelengths.

FIG. 7(a) presents a graph of penetration depth δ, on a logarithmic scale, against atomic number Z, for a range of EUV radiation wavelengths λ. The penetration depth shown is for grazing incidence (α=5°). Compared with X-rays of higher energy (shorter λ), grazing incidence can be achieved at higher angles α in the EUV wavelengths 1-100 nm or 1-150 nm. The phenomenon of "total internal reflection" is familiar in optics at visible wavelengths, where a material such as glass has a refractive index greater than 1. At EUV wavelengths, materials generally have a refractive index less than 1, and the phenomenon of "total external reflection" results. The angle up to which significant reflection can obtained may be referred to as the critical angle. An advantage of the relatively shallow penetration depth at EUV wavelengths is that measurements can be obtained which represent the surface structure of the substrate, without significant interference of buried features which are commonly present in semi-conductor products. As explained further below, this shallow penetration depth greatly facilitates accurate measurement by reconstruction or other techniques.

Figure 7B:
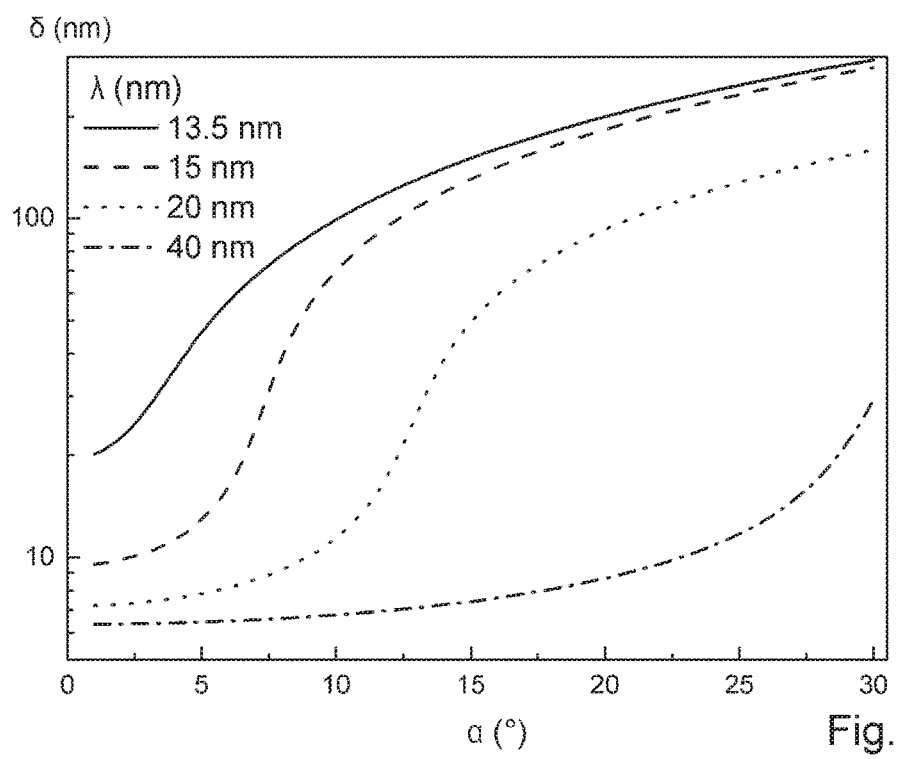

FIG. 7(b) shows variation of penetration depth with angle of incidence for silicon, just as one example material. Particularly for wavelengths in the 15-100 nm range or in the 15-150 nm range, however, penetration of ten or more nanometers can be achieved if desired. For a given structure, a higher penetration depth can be achieved in the direction normal to the substrate, by elevating the angle α of incidence to a higher value. Referring again to FIG. 6, the range of incidence angles available to exploit this effect without losing reflectivity is higher in the EUV range, particularly in the range 15-100 nm or in the range 15-150 nm, than it is for example in X-ray measurement techniques.

Referring to FIG. 8, graphs (a) to (f), illustrate how spectroscopic reflectometry in the EUV wavelength range can yield information on the form of a grating structure (periodic structure) formed on a silicon substrate. In Figures (a) to (c) we compare a silicon grating structure with a plain silicon substrate. In FIGS. 8(d) to (f) we compare two different forms of grating.

Figure 8A:
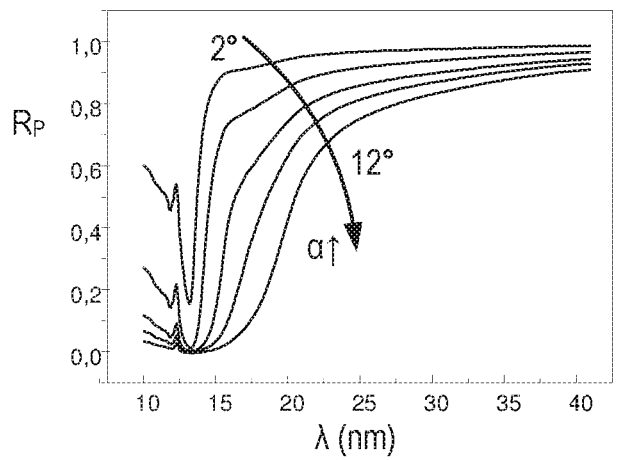
FIG. 8 (a) to (c) comprises graphs of reflectivity over the EUV spectrum, calculated for different angles of incidence, in the case of (a) a plain silicon substrate and (b) a silicon grating structure, with a differences between these reflectivities (a) and (b) being shown at (c)
Figure 8B:
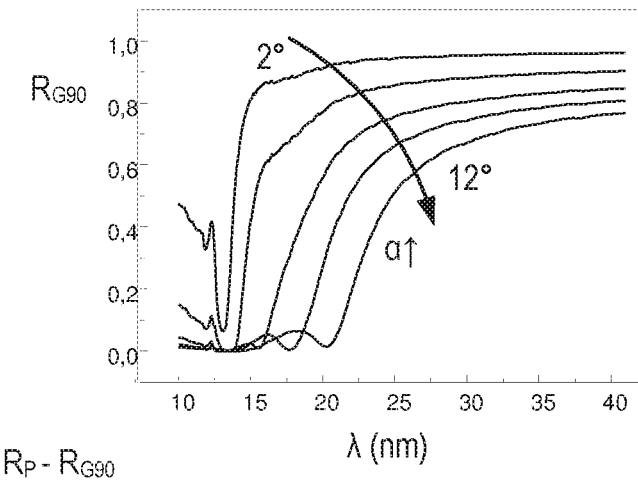

FIG. 8(a) shows calculated reflectivity $R_P$ for a plain silicon wafer across the wavelength range 10 to 40 nm. Each curve is measured at a different incidence angle α, ranging from 2° to 12° in steps. Each curve is a reflection spectrum of the target, as described above. With suitable calibration and normalization, similar reflection spectra will be measured, at least in a particular part of the wavelength range, in the method and apparatus of FIGS. 2 to 5. The period of the grating structure in this example is 200 nm, and the height is 50 nm. The large curved arrow illustrates the trend that can be seen in the shape of the reflection spectrum, ranging from the smallest angle α to the highest. In FIG. 8(b) we see the reflectivity $R_G$ of a target comprising a rectangular grating with period 200 nm and height 50 nm, again made of silicon. Again, reflectivity is plotted over the wavelength range 10 to 40 nm, for a sequence of incidence angles α ranging from 2° to 12°.

Figure 8C:
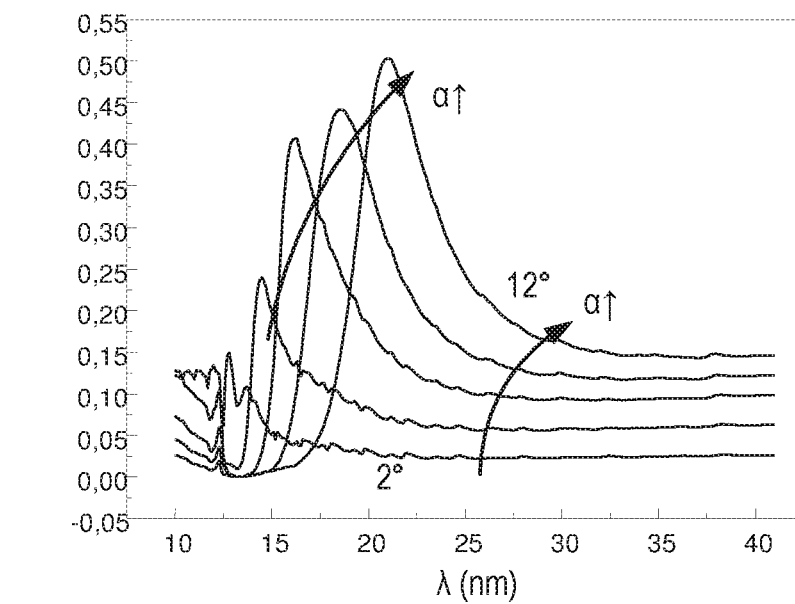
Figure 8D:
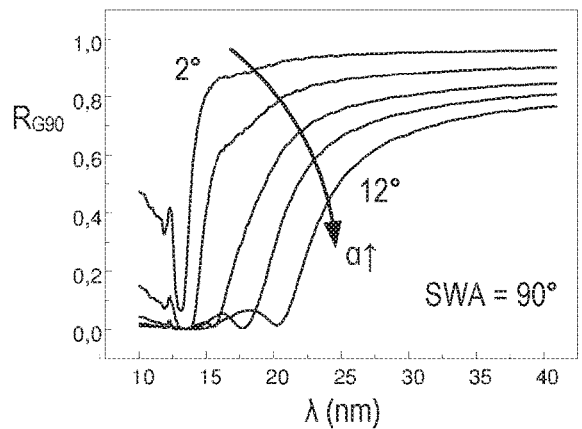
Figure 8E:
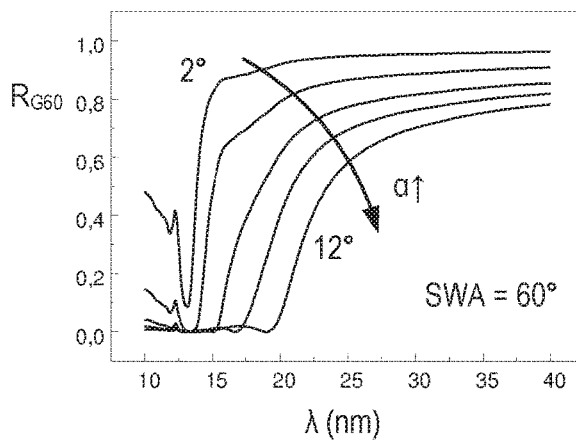
Figure 8F:
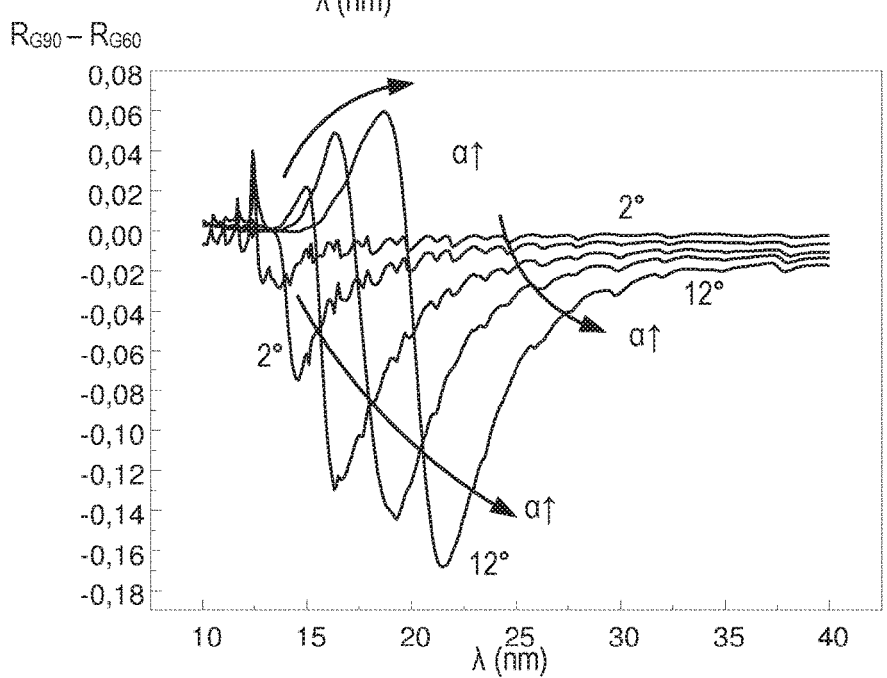

FIG. 8(c) plots the difference between the plain wafer reflectivity of FIG. 8(a) and the grating reflectivity of FIG. 8(b). Particularly in the wavelength range around 15-50 nm, and particularly as the incidence angle rises towards 12°, we see very clearly certain characteristics that can be attributed to the grating structure. In other words, the plot of FIG. 8(c) confirms that good measurement information as to the presence and structure of a grating target should be obtainable by EUV spectroscopic reflectometry using the method and apparatus of FIGS. 2 to 5.

Referring to graphs (d) to (f), we see plots similar to those at (a) to (c). This time, however, the comparison is between the rectangular grating already described (graphs (b) and (d) are the same), and a grating of similar period and height, but with side walls sloping at 60° (graph (e)). Differences between the graphs at (d) and (e) are more subtle than between the graphs at (a) and (b). Nevertheless, when these graphs are subtracted (graph (f)), characteristic features can be seen in the difference, which represent information about the side wall angle of the grating. Again, the strength of the signal is greater as the angle of incidence α increases from 2° to 12°. Accordingly, depending on the material and structure to be measured, it is proposed herein to use angles α of incidence of 5° or greater, for example angles in the range of 10 to 40 degrees. The optimum selection of angle will depend on the availability of spectral components in the source radiation, and on the reflectivity versus angle of incidence of different materials. That is to say, the angle of incidence should be selected as a compromise between the strength of the signals illustrated in the simulations of FIG. 8, and the strength of reflection by the particular materials of a target (FIG. 6. Similarly, the strength of the difference signal (sidewall angle information) varies across the wavelength range. The incidence angle(s) and wavelength range(s) at which measurements will be performed can be selected to define an optimum metrology parameter set for a particular type of target and a particular property of interest.

Figure 9:
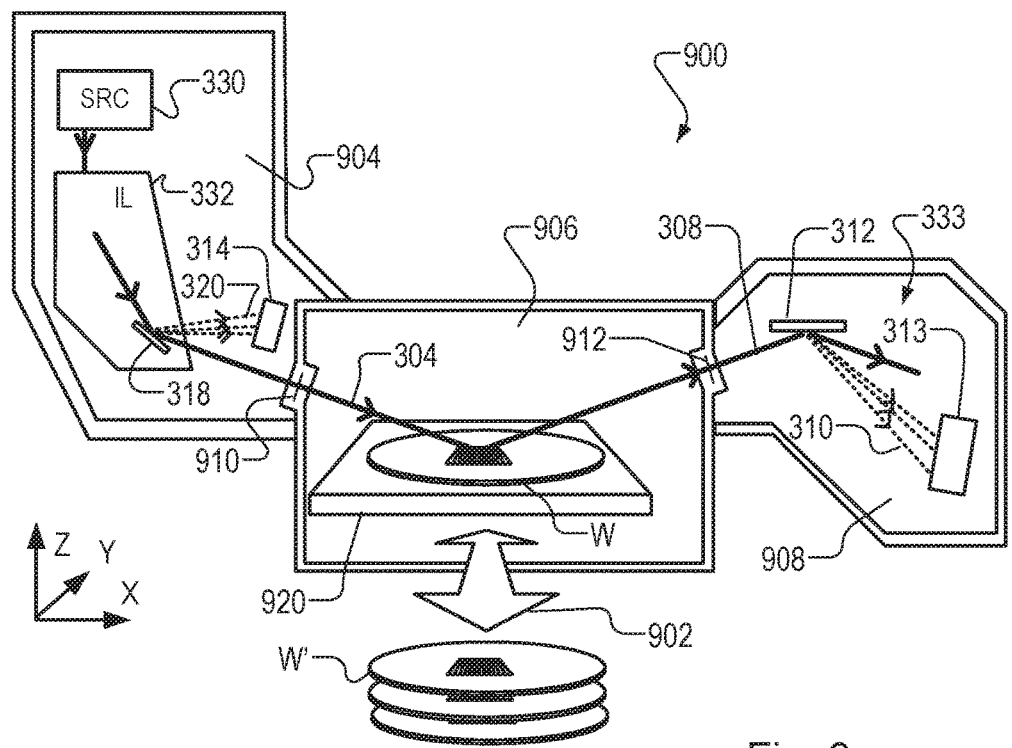
FIG. 9 illustrates the principle of housing components of the apparatus of FIG. 3 in different vacuum or near-vacuum and/or low pressure environments.
Figure 10:
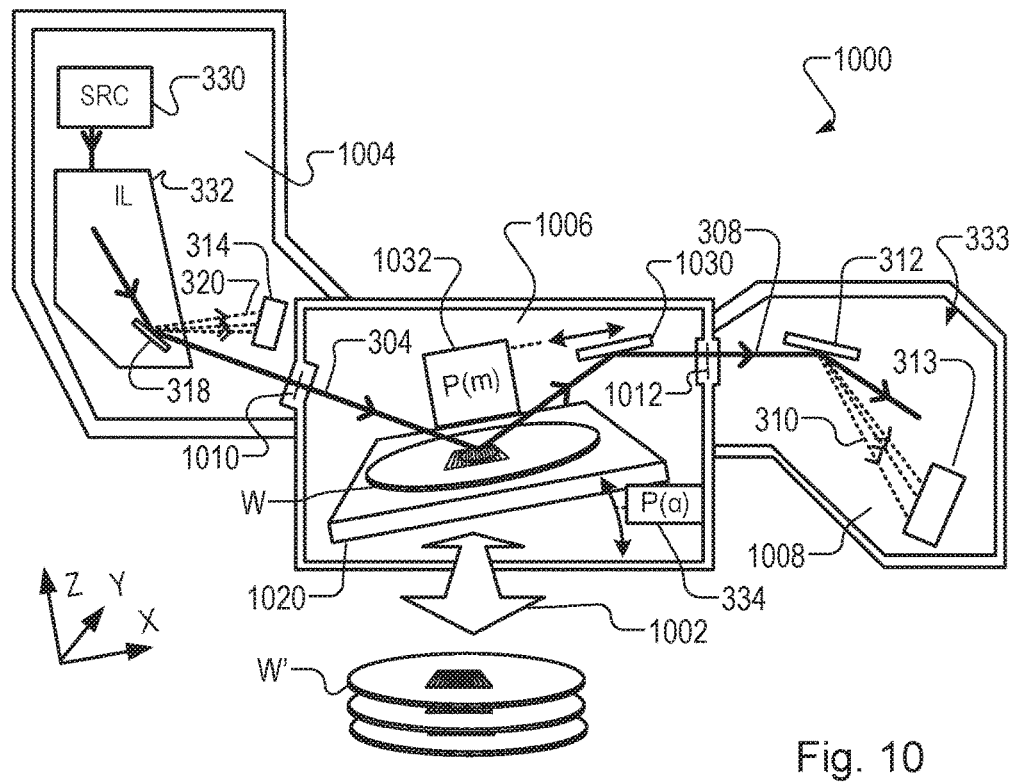
FIG. 10 illustrates a modified principle of housing, including an additional optical element for maintaining a stationary detection system while varying the angle of incidence.

FIG. 9 illustrates schematically the housing of different parts of an EUV metrology apparatus 900. This has features to facilitate management of vacuum and low pressure atmospheres within the apparatus, particularly in a high-volume manufacturing environment. FIG. 10 illustrates a modified metrology apparatus.

Figure 11A:
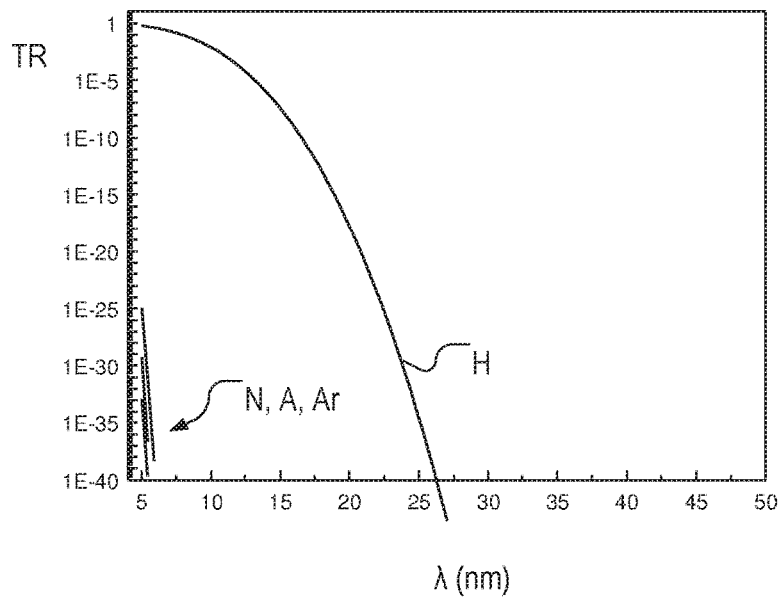
FIG. 11 illustrates the transmission of EUV radiation across the EUV spectrum, through different gaseous atmospheres at (a) atmospheric pressure and (b) 1 millibar.
Figure 11B:
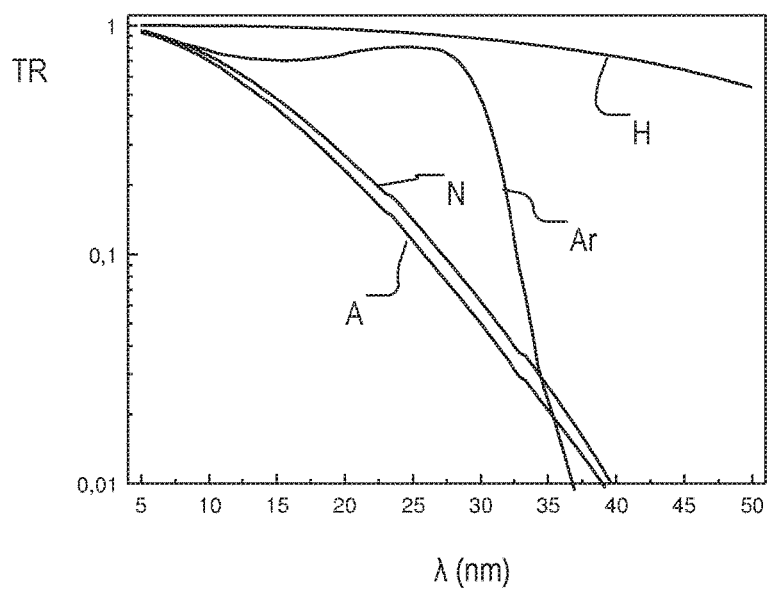

By way of introduction, we refer to the graphs (a) and (b) of FIG. 11. Each graph shows a proportion TR of EUV radiation transmitted across the EUV spectrum, through different gaseous media. The first graph (a) shows the transmission (or rather the lack of transmission) of EUV radiation through 50 cm of various gases at atmospheric pressure. The gases nitrogen (N), air (A), argon (Ar) and hydrogen (H) are represented. Paying attention to the logarithmic scale labeled in steps of $10^{-5}$, it is clear why EUV optical apparatus cannot work in normal atmospheric environments. In the graph (b), however, we see that reasonable transmission is maintained when the atmospheric pressure in the path of the EUV radiation is reduced to 1 millibar. Across the range of 5 to 30 nm, both hydrogen and argon provide relatively good transmission. Even in air and nitrogen, transmission losses may be acceptable. Hydrogen is the easiest for EUV transmission across the entire spectrum of interest. On the other hand, use of hydrogen atmospheres, even at low pressure requires costly safety measures. These factors should all be taken into account in selecting an operating environment before the different parts of the EUV metrology apparatus.

Returning to FIG. 9, an example EUV metrology apparatus is illustrated using the same components and numbering as seen in FIGS. 2 and 3. As already explained with reference to FIG. 11, EUV radiation signals will be severely weakened, unless beam paths are contained within vacuum or low pressure environments. At the same time, if the apparatus is to be used in a high volume manufacturing environment, operations represented schematically at 902 will be performed frequently to exchange a substrate W currently within the apparatus with a new substrate W'. In the event that the entire apparatus would be housed in a vacuum environment, the cost and time delay required to re-establish the vacuum environment after loading and unloading a wafer or bath of wafers would seriously degrade throughput. At the same time, it may be desirable to have as much as possible of the beam paths in a high vacuum environment.

For this reason, in example metrology apparatus 900, different parts of the EUV optical system are contained in different chambers 904, 906, 908. Suitable walls define these chambers, while windows 910 and 912 permit EUV radiation to pass between the chambers. The first chamber 904 contains the source 330 and illumination system 332. A first atmospheric condition, for example high vacuum, is maintained in chamber 904 by suitable pumping and control systems, not shown. First window 910 permits incident beam 304 to enter the second chamber 906, where the target is supported on a substrate support W. In the second chamber 906 a second atmospheric condition is maintained surrounding the target. The second atmospheric condition may be, for example, a low pressure gaseous atmosphere, for example using one of the atmospheres indicated in FIG. 11(b). In this way, when substrates W and W' are exchanged through some form of air lock mechanism, the required atmospheric condition can be established and re-established relatively quickly, and without undue cost. While transmission losses in the second atmospheric condition may be one order of magnitude greater than in high vacuum, for the limited distance of travel and the operational productivity, these losses can be tolerated.

In this example, components of detection system 333 such as grating 312 and detector 313 are located in a third chamber 908, which is maintained at a third atmospheric condition. The third atmospheric condition may be for example a high vacuum. A second window 912 permits the reflected ray 308 to enter the detection system in chamber 908, carrying spectroscopic information about a target on the substrate.

It may be noted that, if the windows 910 and 912 are of limited extent, then the geometry of the apparatus 900 in this example greatly restricts the range of incidence angles α that may be employed. FIG. 10 illustrates a variant of the FIG. 9 apparatus, in which this problem is addressed by an additional mirror component. Other approaches may also be considered, for example by providing a number of discrete windows appropriate to different incidence angles, and/or by housing at least some components of the detection system within the same chamber 906 as the sample, so that they may move without losing their line of sight through a window.

FIG. 10 shows a EUV metrology apparatus 1000 which is a modified version of the apparatus 900 of FIG. 9. Core components of the metrology apparatus are again numbered 300 to 332, just by way of example. Other features relating to the housing and mounting of the apparatus are numbered the same as in FIG. 9, but with prefix "10" instead of "9". Thus, chambers 1004, 1006 and 1008 are provided, for example, which communicate optically through windows 1010 and 1012.

As also seen in FIG. 3, substrate support 1020 in this example is movable by an actuator 334, to vary the incidence angle α at which the rays 304 impinge on the grating target. By this measure, the source and illumination system, as well as the beam 304 follow a fixed path. This is good for the stability of the source and optical system, as well as allowing window 1010 to remain in a fixed position. On the other hand, additional elements in this example also allow a wide range of incidence angles to be accommodated, while the second window 1012 and the detection components 312 etc. also remain in fixed positions. To achieve this, an additional mirror element 1030 is provided, which is a plane mirror having its reflecting surface parallel to the plane of substrate W. By simple geometry and maintaining this parallel relationship between the 1030 and substrate W, it is achieved that the original variation of 2α in the direction of the reflected ray is cancelled out. Mirror 1030 may be a single large mirror held in proximity to and parallel to the substrate so that a different part of the mirror catches the reflective ray at a different incidence angle. Alternatively, a smaller mirror 1030 may be provided, with an actuator 1032 which effects a translation movement of the mirror, as the incidence angle varies.

Figure 12:
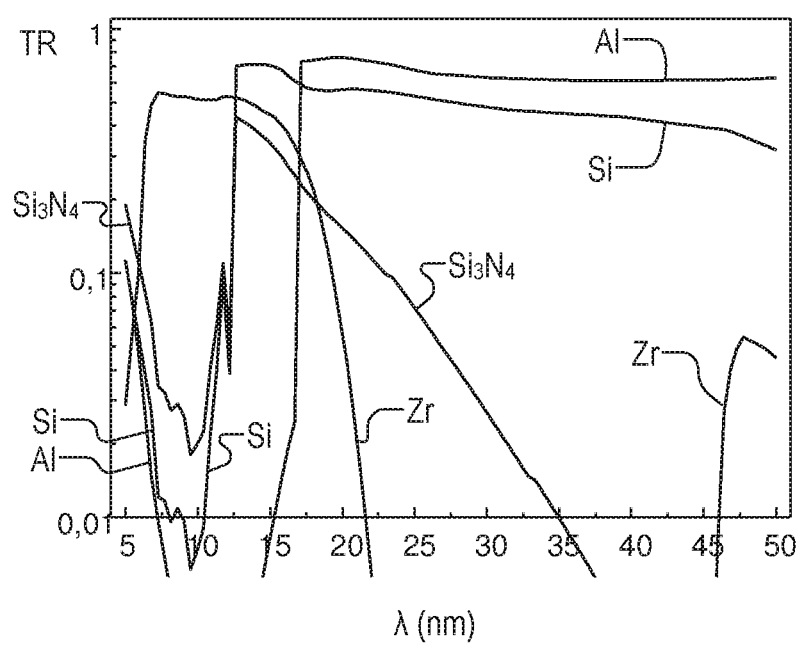
FIG. 12 illustrates the transmission of EUV radiation through windows of different materials, given a 200 nm thickness.

Referring to FIG. 12, the graph shows that different window materials have different transmission properties over the spectrum of EUV radiation. The graph shows on a log scale a proportion TR of radiation transmitted through a window formed by a 200 nm membrane of each material. As can be seen, it is very challenging to provide windows that are transparent over a large range of EUV wavelengths. Whether a window is used, and what type of window is used, will depend on the alternative arrangements that may be made to manage the atmosphere in each part of the apparatus. As an alternative to a physical membrane isolating the different compartments 904/1004, 906/1006, 908/1008, open ports communicating between the different compartments can be envisaged, which are simply made small enough that a useful pressure differential can be maintained across them. Thus, while window membranes are schematically indicated at 910/1010 and 912/1012, either or both of these membranes can be replaced by an open aperture that may be sized adequately to permit all of the wanted radiation to pass, whilst being small enough to restrict as far as possible the flow of gas from one compartment to the next. Where a physical membrane is designed for one or both windows, membranes with higher transmittance than the ones represented in FIG. 12 can be developed. A particular example is described by Pekka Törmä et al in a paper "Performance and Properties of Ultra-Thin Silicon Nitride X-ray Windows", IEEE Transactions on Nuclear Science, VOL. 61, NO. 1, February 2014. That paper describes an ultra-thin window membrane, formed of a silicon nitride material down to 20 nm thickness with additional supporting structures. While that paper generally concerns shorter wavelength radiation, there is overlap between the low-energy range of the X-ray spectrum and the shorter wavelengths of the EUV spectrum.

Figure 13:
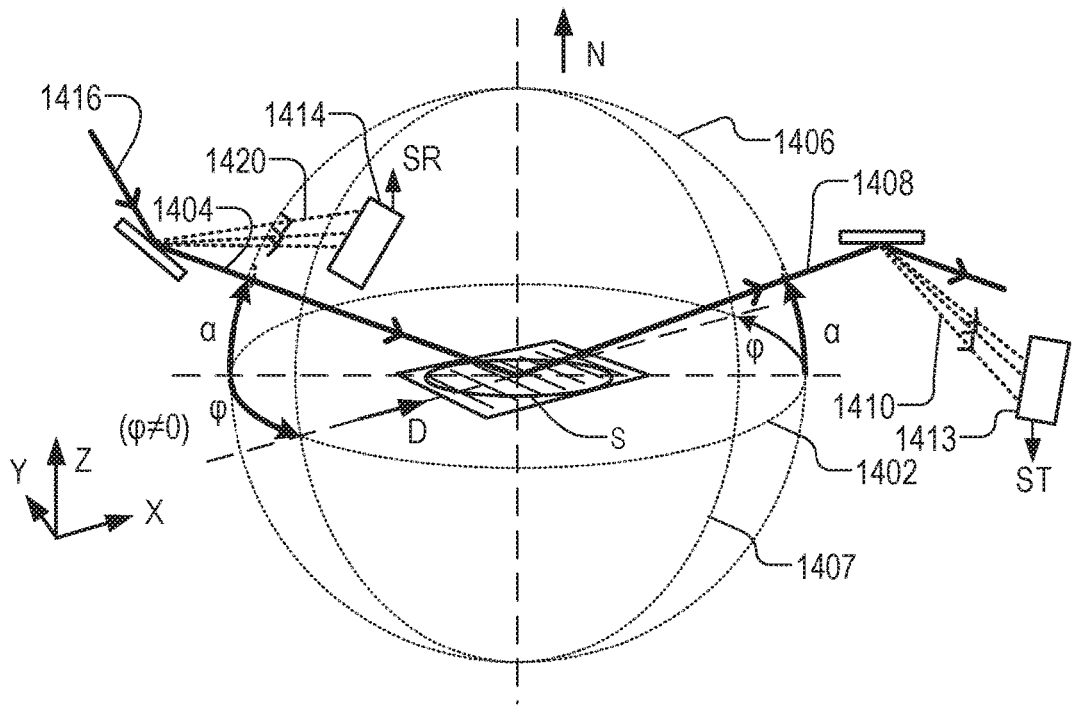
FIG. 13 illustrates the geometry of incident and reflected rays in relation to a grating target in a metrology method according to a second embodiment of the present invention in which a non-zero azimuthal angle is used.
Figure 14:
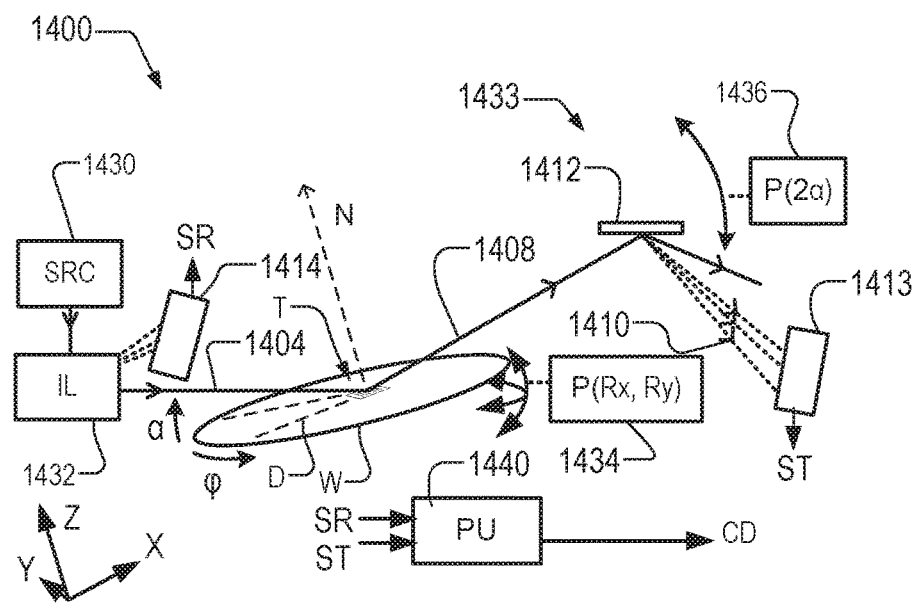
FIG. 14 illustrates schematically the components of a metrology apparatus, performing the method of FIG. 13.

FIG. 13 illustrates a modified metrology method and FIG. 14 illustrates a corresponding metrology apparatus 1400. Components labeled '14xx' in these examples should be considered to be the same as those labeled '3xx' in the FIG. 3 apparatus, unless mentioned otherwise. Thus the modified apparatus includes, for example, an illumination system 1430, illumination system 1432 and detection system 1433. Compared with the apparatus of FIG. 2, however, positioning system 1434 is operable so that the angle of incidence of incident ray 1404 can be varied not only in a grazing incidence angle α, but also in an azimuthal angle, here labeled φ.

Again, an X, Y, Z coordinate system is defined relative to the substrate. Again, target T is assumed to comprise a one-dimensional grating with direction of periodicity D parallel to the X axis of the substrate. Again, the substrate and target can be tilted to vary the angle of incidence. However, a non-zero azimuthal angle of incidence φ is allowed. The azimuthal angle φ is defined relative to the direction of periodicity D of the grating target T. (In the case of a two-dimensionally periodic target, D may be either of the principal directions of periodicity.) That is to say, when the direction of incidence is projected onto the plane of the substrate, the azimuthal angle φ between the incident ray and the direction of periodicity D is non-zero, and may be very substantial. That is to say, the direction of irradiation lies outside a plane defined by the direction of periodicity D and the direction N normal to the substrate. Rather, the incident ray travels in a plane oblique to the direction of periodicity D. The oblique plane is represented by a circle 1407 that is orthogonal to the plane of the substrate but oblique to the direction of periodicity and the X-Z plane. It will be understood that, while the choice of labels of planes and axes is arbitrary, the grazing incidence angle and azimuthal angle are defined with reference to physical properties of the periodic structure of the target. The inventor has recognized that the diffraction efficiency of different diffraction orders can be increased substantially when non-zero azimuthal angles are used. This in turn has an impact on the spectrum of the reflected (zero order) ray 1408.

In implementing the apparatus 1400, different arrangements of positioning system can be used to achieve the non-zero azimuthal angle. Reference 1434 indicates a positioning subsystem with actuators for rotation about the X and Y axes of the substrate. For a desired combination of grazing incidence angle α and azimuthal angle φ, appropriate command values Rx and Ry are calculated to cause tilting of the substrate in two dimensions to achieve the desired angles. In another implementation, actuators may be provided for rotation and tilting, directly driving the angles α and φ. As will be appreciated from FIG. 14, rotation Rz corresponds directly to a desired azimuthal angle φ, and command values in this case can be generated more directly from the desired measurement angles.

In other areas of metrology, the type of mounting required to vary both the grazing incidence (polar) angle and the azimuthal angle is known as a "conical mount", and that term can be adopted in this EUV reflectometry apparatus also. In general, the skilled reader will appreciate that any form of command and any form of actuating mechanism can be used to implement this example, provided it is suitable to achieve a known non-zero azimuthal angle of incidence. It will also be understood that the relative orientation of the direction of incidence and the target is what matters (and of course the correct X-Y positioning of the target relative to the radiation spot S).

As mentioned above, the use of non-zero azimuthal angles may allow enhanced diffraction efficiency using the conical mount of FIGS. 13 and 14, compared with the FIGS. 2 and 3 arrangement. This may in turn provide stronger signals for measurement of particular properties, reducing measurement time and/or increasing measurement accuracy. Another benefit of using a non-zero azimuthal angle can be seen already in FIG. 13, by comparison with FIG. 2. Notice that the spot S, if it becomes elongated because of the oblique angle of incidence, is elongated in a direction defined by the azimuthal angle. Therefore the longest dimension of the spot is aligned with a diagonal direction of the target. Given that the majority of targets will be rectangular in shape, this diagonal elongation of the spot in fact allows a larger spot overall to be fitted within the target area. Consequently, for a given illumination intensity, a greater overall power of measurement radiation can be directed at the target and so the signal at detector will be proportionately increased. This effect alone may allow a slight shortening in measurement time. Alternatively, or in addition, focusing tolerance may be relaxed, which also shortens measurement time.

Figure 15:
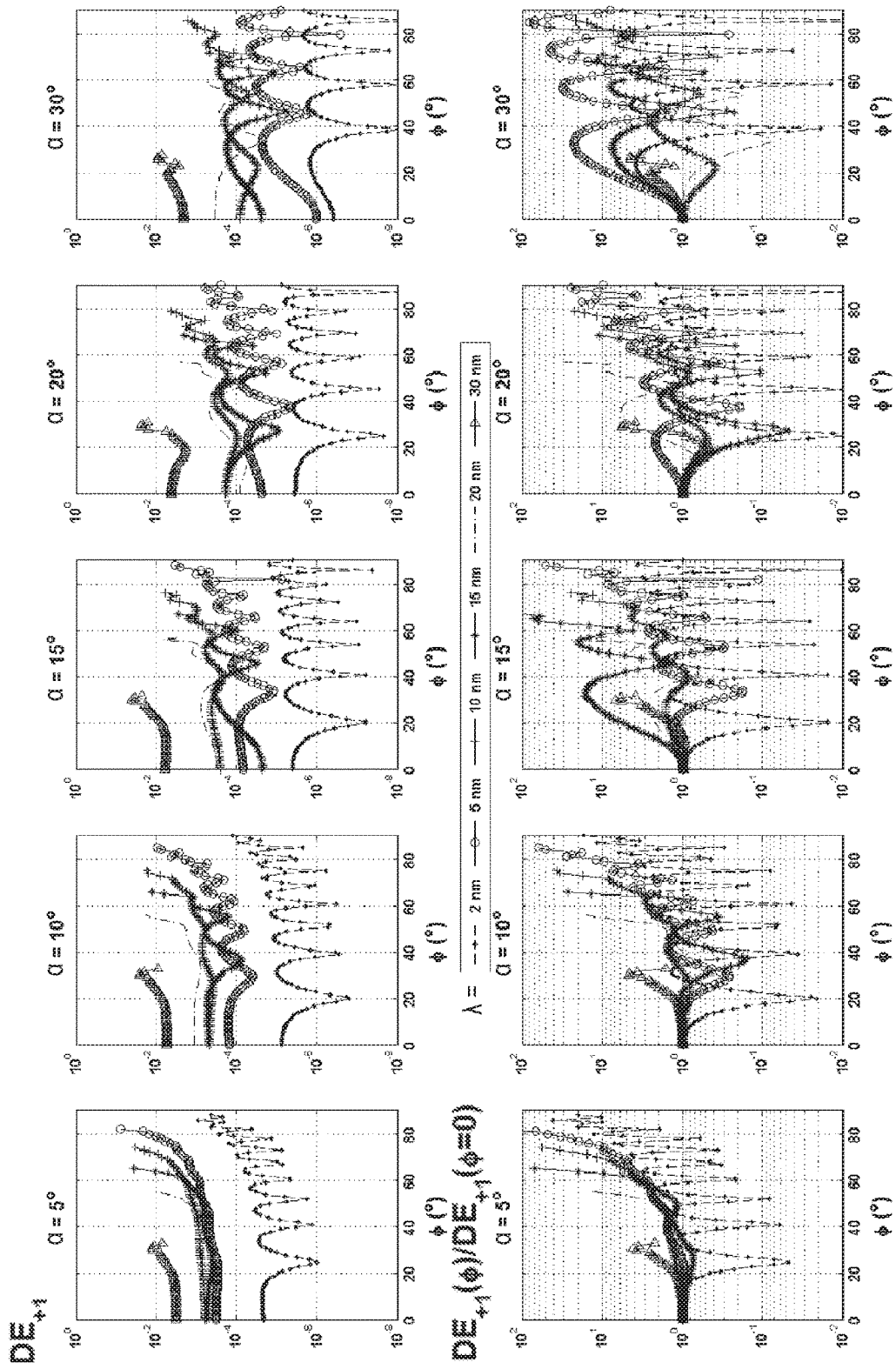
FIG. 15 illustrates the variation of first order diffraction efficiency for different grazing incidence angles and wavelengths as a function of azimuthal angle for an example target in the method of FIGS. 13 and 14.

FIG. 15 illustrates the variation of first order diffraction efficiency $DE_{+1}$ for different grazing incidence angles and wavelengths as a function of azimuthal angle for an example target in the method of FIGS. 13 and 14. Each design of target, with its different structures and materials, will exhibit its own particular set of diffraction efficiencies, and its own set of variations in the way the reflection spectra vary with azimuthal angle φ (and grazing angle α). The target in this example is a grating with pitch 18 nm. In the five graphs on the top row, the vertical axis represents diffraction efficiency on a log scale, and the horizontal axis represents the azimuthal angle φ, ranging from zero to 90°. Each graph corresponds to a different grazing incidence angle α as marked. Within each graph, diffraction efficiency is plotted for a number of wavelengths 2, 5, 10, 20 and 30 nm. The bottom row of five graphs present the same data in another form, where the diffraction efficiency at each wavelength is normalized relative to its value at zero azimuthal angle. It can be seen that, especially at the shorter wavelengths and/or higher incidence angles, the first order diffraction efficiency (and by implication the zero order signal captured by detector 1413) is strongly dependent on azimuthal angle. By choosing one or more, especially two or more azimuthal angles for measurements, more particular information can be obtained on the target structure.

Figure 16:
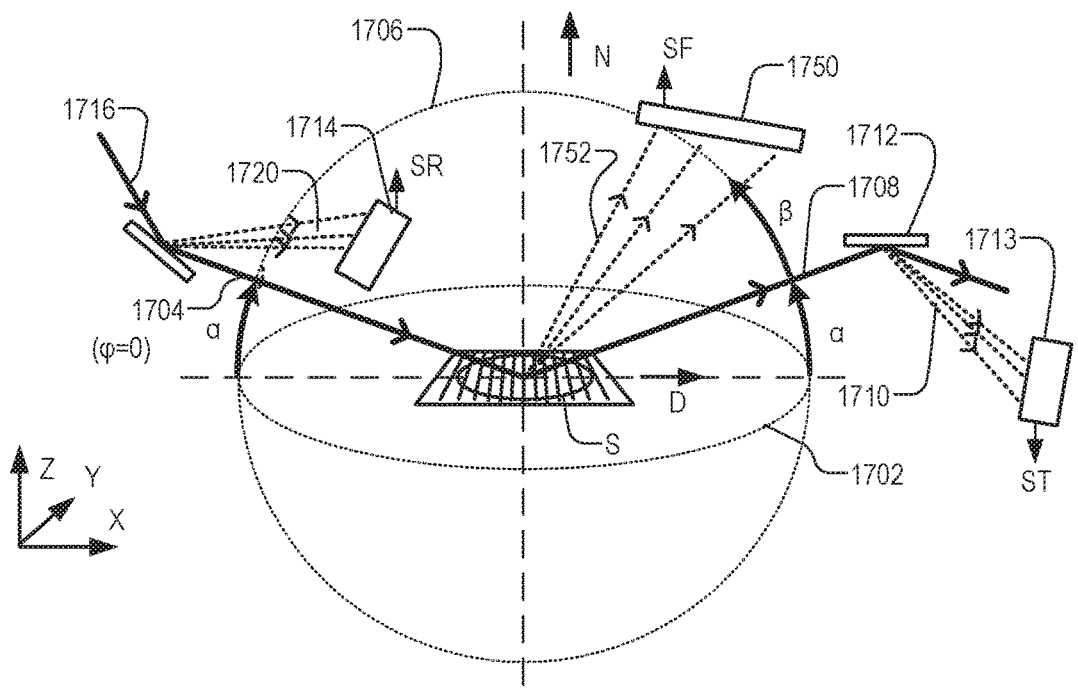
FIG. 16 illustrates the geometry of incident and reflected rays in relation to a grating target in a metrology method according to a third embodiment of the present invention in which first order diffracted radiation from the grating target is also measured.
Figure 17:
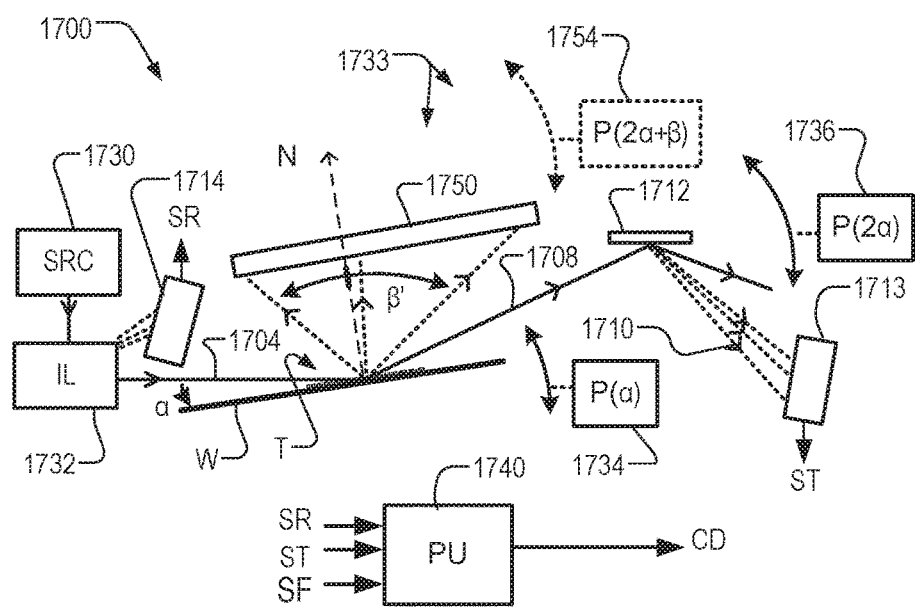
FIG. 17 illustrates schematically the components of a metrology apparatus, performing the method of FIG. 16.

FIG. 16 illustrates a further modified metrology method and FIG. 17 illustrates a corresponding metrology apparatus 1700. Components labeled '17xx' in these examples should be considered to be the same as those labeled '3xx' in the FIG. 3 apparatus, unless mentioned otherwise. Thus the modified apparatus includes, for example, an illumination system 1730, illumination system 1732 and detection system 1733.

Again, an X, Y, Z coordinate system is defined relative to the substrate. Again, target T is assumed to comprise a one-dimensional grating with direction of periodicity D parallel to the X axis of the substrate. Again, the substrate and target can be tilted to vary the angle of incidence. Detection system 1733 again comprises a diffraction grating 1712 to split the reflected rays 1708 into a spectrum 1710 of different wavelengths. The reflection spectrum 1710 is captured by detector 1713 and signals ST are provided to processor 1740.

In addition, in this modified method and apparatus, a third detector 1750 is provided to receive another spectrum 1752. Spectrum 1752 comprises radiation diffracted at first order by the periodic structure of the target T. The angle β at which the first order diffracted radiation is directed depends on the pitch of the target grating as well as the wavelength of the diffracted radiation. In the case of spectroscopic EUV reflectometry, where the incident radiation comprises a range of wavelengths, then radiation diffracted by the target spreads into a spectrum at a range of angles β, as shown. This first order spectrum, like the reflection spectrum 1710, contains information about the target structure. Signals SF which are captured by detector 1750 are supplied to processor 1740 for use (together with signals SR and ST), in calculating an improved measurement of a property of interest of the target.

Capturing first order diffraction spectra may have particular benefit in resolving properties of the target which are associated with asymmetry.

While the range of angles β is shown as quite a narrow range in FIG. 16, for convenience, it will be understood that quite a wide range of angles, including "backwards" diffraction, may be encountered. This is particularly the case because (i) the range of wavelengths of interest may span more than one octave (for example the ranges 10 to 40 nm or even 5 to 50 nm are mentioned in the examples above) and (ii) the pitch of the finest target gratings (which may be product features) will be similar in magnitude to the wavelength of the radiation, in a number of potential applications. FIG. 17 illustrates this range of angles. Referring to angle β', defined relative to the normal direction N, a range of angles from −90° to +20° may be expected to arise, for example.

In order to accommodate wide variations in the diffraction angle β (or β'), a further actuator 1754 may be provided to move the detector 1750 to an appropriate position, as the grazing incidence angle α varies by actuator 1734 and as the first order diffraction angle β varies with grating pitch and wavelength. Alternatively or in addition, detector 1750 may be made large in extent, and/or placed close to the substrate in the vicinity of the target. This is shown schematically in FIG. 17. Collimating optics may optionally be provided to reduce the spread of angles, if desired, so that they can be captured on a conveniently sized and conveniently placed detector 1750.

Figure 18:
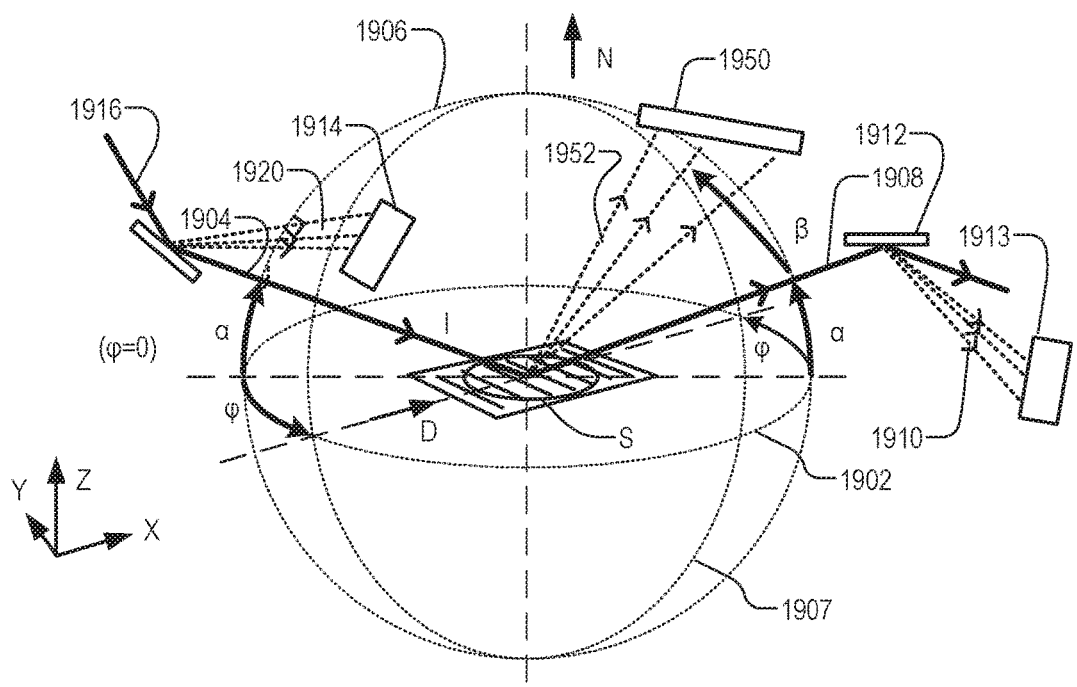
FIG. 18 illustrates the geometry of incident and reflected rays in relation to a grating target in a metrology method according to a fourth embodiment of the present invention, combining features of the second and third embodiments.
Figure 19:
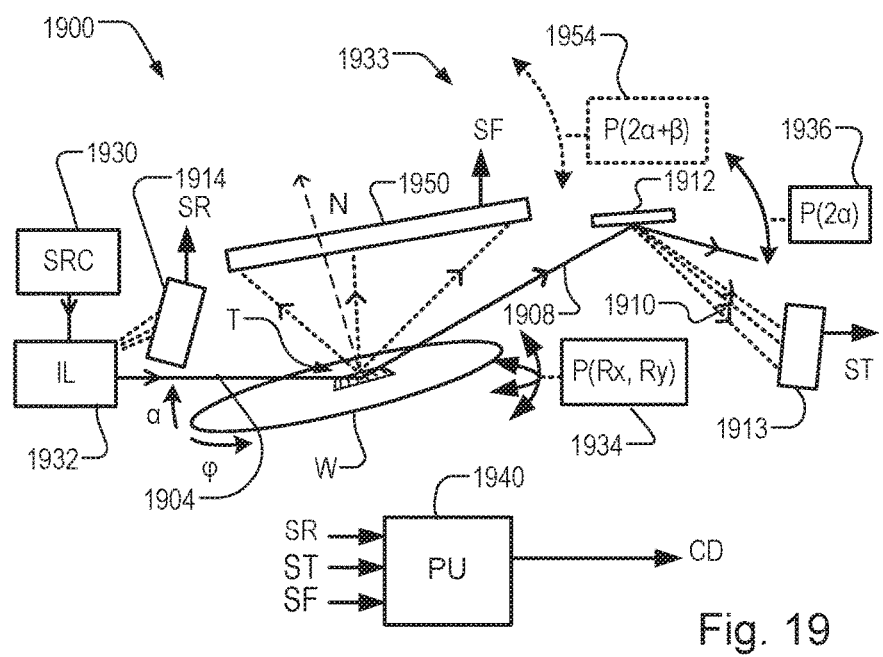
FIG. 19 illustrates schematically the components of a metrology apparatus, performing the method of FIG. 18.

FIG. 18 illustrates a further modified metrology method and FIG. 19 illustrates a corresponding metrology apparatus 1900. This method and apparatus combine the modifications already described above with reference to FIGS. 13 and 14 (non-zero azimuthal angle) and FIGS. 16 and 17 (using first order diffraction from the target grating). Components labeled '19xx' in these examples should be considered to be the same as those labeled '14xx' and/or '17xx' in the methods and apparatuses of FIGS. 13/14 and 16/17. Thus the modified apparatus includes, for example, an illumination system 1930, illumination system 1932 and detection system 1933.

Again, an X, Y, Z coordinate system is defined relative to the substrate. Again, target T is assumed to comprise a one-dimensional grating with direction of periodicity D parallel to the X axis of the substrate. Again, the substrate and target can be tilted to vary the angle of incidence. Detection system 1933 again comprises a diffraction grating 1912 to split the reflected rays 1908 into a spectrum 1910 of different wavelengths. The reflection spectrum 1910 is captured by detector 1913 and signals ST are provided to processor 1940.

As in the example of FIGS. 13 and 14, a non-zero azimuthal angle of incidence φ is allowed. Reference 1934 indicates a positioning subsystem with actuators for rotation about the X and Y axes of the substrate. The discussion above relating to FIGS. 13 to 15 applies equally in the method and apparatus of FIGS. 18 and 19.

In addition, in this modified method and apparatus, a third detector 1950 is provided to receive another spectrum 1952. Spectrum 1952 comprises radiation diffracted at first order by the periodic structure of the target T. Signals SF representing the first order diffraction spectrum of target T are provided to processor 1940. The discussion above relating to FIGS. 16 and 17 applies equally in the method and apparatus of FIGS. 18 and 19. The diffraction efficiencies of FIG. 15 determine directly to the strength of the detected signals SF at each wavelength.

Application Example

Any of the apparatuses 300, 900, 1000, 1400, 1700, 1900 can be used as EUV metrology apparatus 244 in a lithographic manufacturing system such as is illustrated schematically in FIG. 1.

Figure 20:
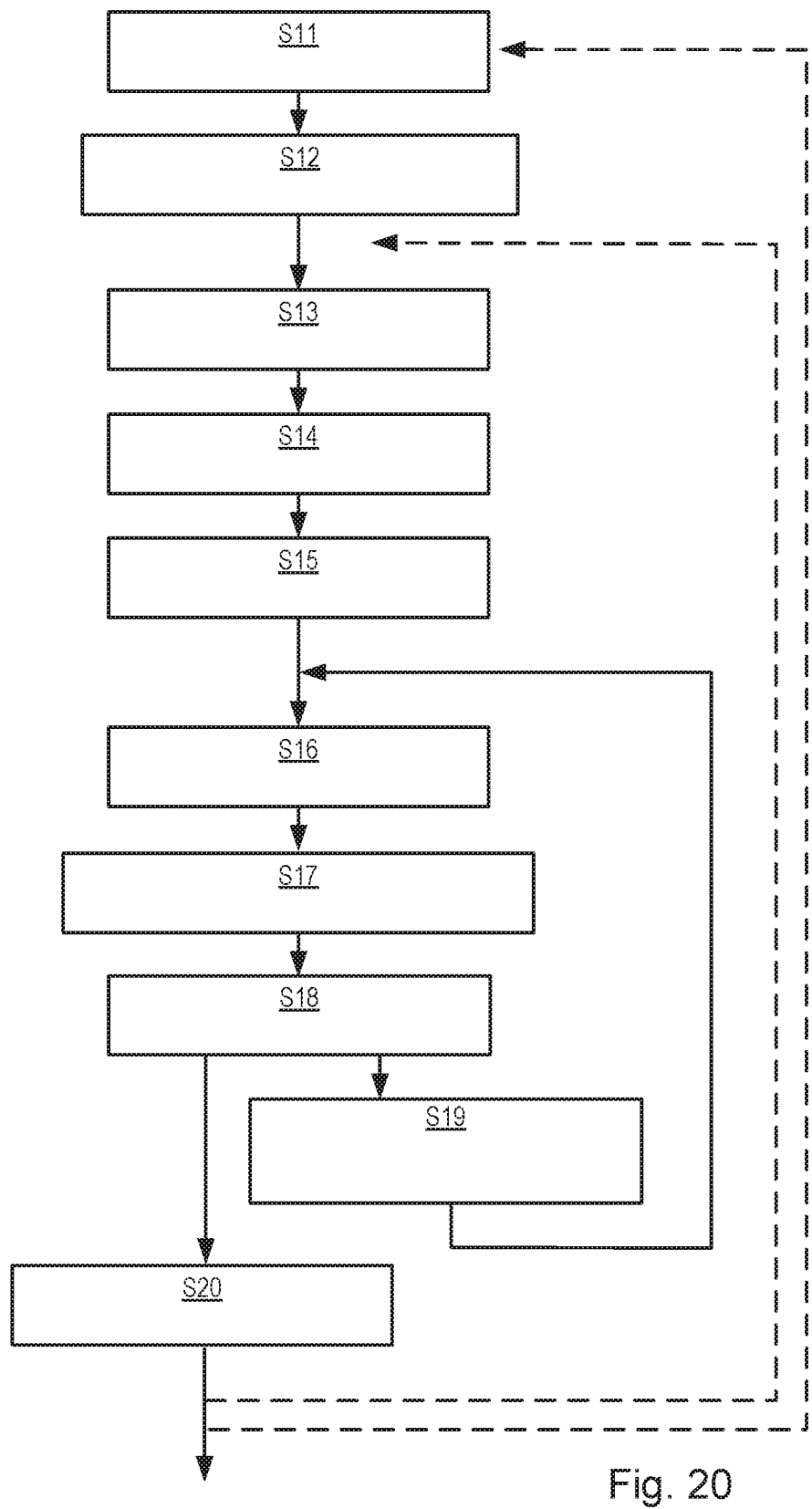
FIG. 20 is a flow chart illustrating a metrology method according to an embodiment of the present invention.

FIG. 20 is a flowchart of a method of measuring parameters of a target structure, using the EUV metrology techniques disclosed herein. As described above, the target is on a substrate such as a semiconductor wafer. This target will often take the shape of a periodic series of lines in a grating or structures in a 2-D array. The purpose of the metrology techniques is to calculate measurements of one or more parameters of the shape. In reconstruction technique, rigorous optical theories are used effectively to calculate what values of these parameters will result in a particular observed reflection spectrum (optionally including spectra of one or more higher diffraction orders). In other words, target shape information is obtained for parameters such as CD (critical dimension) and overlay. CD, or critical dimension, is the width of the object that is "written" on the substrate and is the limit at which a lithographic apparatus is physically able to write on a substrate. In some situations, the parameter of interest may be CD uniformity, rather than an absolute measurement of CD itself. Other parameters such as grating height and side wall angle may also be measured, if desired. Overlay metrology is a measuring system in which the overlay of two targets is measured in order to determine whether two layers on a substrate are aligned or not.

Using results from EUV metrology apparatus 244 in combination with modeling of a target structure such as the target 30 and its reflection and/or diffraction properties, measurement of the shape and other parameters of the structure can be performed in a number of ways. In a first type of process, represented by FIG. 9, a diffraction pattern based on a first estimate of the target shape (a first candidate structure) is calculated and compared with the observed reflection spectra. Parameters of the model are then varied systematically and the reflection spectra re-calculated in a series of iterations, to generate new candidate structures and so arrive at a best fit. In a second type of process, reflection spectra for many different candidate structures are calculated in advance to create a 'library' of reflection spectra. Then the reflection spectrum observed from the measurement target is compared with the library of calculated spectra to find a best fit. Both methods can be used together: a coarse fit can be obtained from a library, followed by an iterative process to find a best fit. It is expected that in EUV spectroscopic reflectometry the computation for the first type of process will not be burdensome. That being the case, there would be no need to resort to a library process.

Referring to FIG. 20 in more detail, the way the measurement of the target shape and/or material properties is carried out will be described in summary. The following steps are performed. The steps will be listed here, and then explained in more detail:

S11: Receive Substrate with Target(s)
S12: Define Measurement Recipe (α,φ)
S13: Measure EUV Reflection Spectrum or Spectra
S14: Define Model Recipe
S15: Estimate Shape Parameters
S16: Calculate Model Reflection Spectrum or Spectra
S17: Compare Measured v Calculated Spectra
S18: Calculate Merit Function
S19: Generate Revised Shape Parameters
S20: Report Final Shape Parameters The steps are not necessarily performed exactly in the above order, and the skilled person will appreciate that certain steps can be performed in a different order without affecting the result.

At S11 a substrate W is received with one or more metrology targets T upon it. The target will be assumed for this description to be periodic in only one direction (1-D structure). In practice it may be periodic in two directions (2-dimensional structure), and the processing will be adapted accordingly. At S12 a measurement recipe is defined, which in the enhanced method defines a range of one or more incidence angles α at which spectra are to be taken, and optionally defines a non-zero azimuthal angle φ. The optimum azimuthal angle for each type of target structure and manufacturing process can be determined by prior experiment and/or computational simulation. A recipe can be defined which measures a target using with two or more azimuthal angles, if desired. Graphs like those shown in FIG. 15 can be used to select the value or values of azimuthal angle that give the best combination of diffraction efficiencies across the diffraction orders of most interest. Alternatively, measurements of each target can be made with a single (zero or non-zero) value for the azimuthal angle φ, and a range of different incidence angles α.

At S13 with a target structure positioned at the spot S, reflection spectra of the actual target on the substrate are measured using EUV radiation in an apparatus such as is illustrated in any of FIGS. 3, 5, 9, 14, 17 and 19. The measured reflection spectra 310 (optionally including first order diffraction spectra 1752, 1952) are captured by detector 313 forwarded to a calculation system such as processor 340. Before being used in further calculations, the spectra are normalized according to pre-stored calibration values and according to the reference spectrum recorded by detector (314, 1414, 1714, 1914). In practice, a number of reference spectra and target spectra will be recorded over several pulses of radiation, each target spectrum being normalized to the reference spectrum from the same pulse before being added into a measured target spectrum. Each measured target spectrum corresponds to an incidence angle α (and optionally a non-zero azimuthal angle φ). To obtain a robust measurement through reconstruction, several spectra of the same target may be captured with different incidence angles α or different azimuthal angle φ to increase diversity of information.

Note that the reflection spectra may be processed as detailed spectra, or they may be simplified into a set of parameters before being used in calculations. As a particular example, the reflection spectrum may be reduced simply to a set of values representing the intensity of identifiable spectral features (peaks or lines). The intensity may be obtained for example by identifying a peak in the reflection spectrum that corresponds to a respective peak in the incident radiation, and assigning to that peak a value corresponding to the height of the observed peak.

At S14 a 'model recipe' is established which defines a parameterized model of the target structure in terms of a number of parameters $p_i$ ($p_1$, $p_2$, $p_3$ and so on). These parameters may represent for example, in a 1-D periodic structure, the angle of a side wall, the height or depth of a feature, the width of the feature. Properties of the target material and underlying layers are also represented by parameters such as refractive index (at each particular wavelength present in the EUV radiation beam). Importantly, while a target structure may be defined by dozens of parameters describing its shape and material properties, the model recipe will define many of these to have fixed values, while others are to be variable or 'floating' parameters for the purpose of the following process steps. For the purposes of describing FIG. 20, only the variable parameters are considered as parameters $p_i$.

Because of the shallow penetration depth of EUV radiation, the need to provide floating parameters representing underlying layer properties can be lower than in the case of optical metrology with longer wavelengths. Consequently, the EUV spectroscopic metrology disclosed herein can provide measurements that are more robust against process variations than optical CD metrology tools, for a given level of computational complexity.

At S15 a model target shape is estimated by setting initial values $p_i(0)$ for the floating parameters (i.e. $p_1(0)$, $p_2(0)$, $p_3(0)$ and so on). Each floating parameter will be generated within certain predetermined ranges, as defined in the recipe.

At S16, the parameters representing the estimated shape, together with the properties of the different materials in the model, are used to calculate the scattering properties, for example using a rigorous computational method such as RCWA or any other solver of Maxwell equations. This gives an estimated or model reflection spectrum of the estimated target shape, for each angle α (or combination of angles α and φ).

At S17 and S18 the measured reflection spectra and the model reflection spectra are then compared and their similarities and differences are used to calculate a "merit function" for the model target shape.

Assuming that the merit function indicates that the model needs to be improved before it represents accurately the actual target shape, control passes to step S19 where new parameters $p_1(1)$, $p_2(1)$, $p_3(1)$, etc. are estimated and fed back iteratively into step S16. Steps S16 to S18 are repeated. In order to assist the search, the calculations in step S16 further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

When the merit function indicates that this iterative process has converged on a solution with a desired accuracy, control passes to step S20 and the currently estimated parameters (for example a CD value) are reported as the measurement of the actual target structure.

The computation time of this iterative process is largely determined by the model used, in other words by the calculation of an estimated model spectrum using a rigorous diffraction theory from the estimated target structure. If more parameters are required, then there are more degrees of freedom. The calculation time increases in principle with the power of the number of degrees of freedom. The estimated or model spectrum calculated at S16 can be expressed in various forms. Comparisons are simplified if the calculated pattern is expressed in the same form as the measured spectrum generated in step S13. Once the value for one target has been calculated, a new target on the same substrate or a similar substrate may be measured using the same steps S13 etc., without changing the measurement recipe. Where a different type of substrate or target is to measured, or in any case where it is desired to change the measurement recipe, control passes to step S11 or S12 instead.

Figure 21:
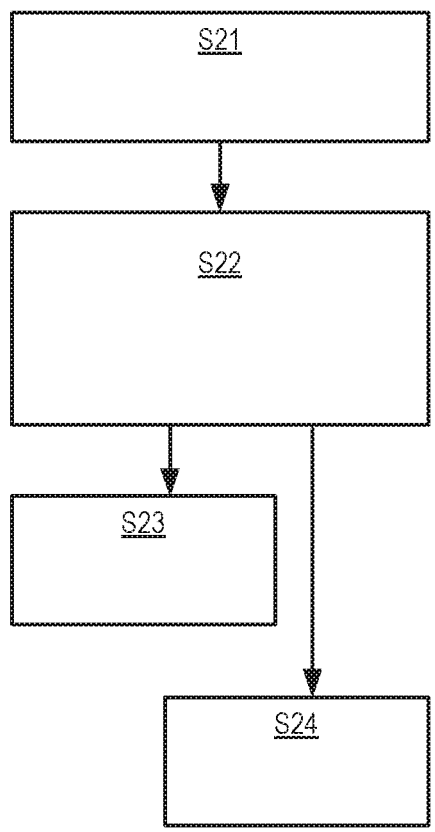
FIG. 21 is a flow chart illustrating a method of controlling performance of a metrology method and/or of a lithographic manufacturing process using measurements made by the method of FIG. 20.

FIG. 21 illustrates the application of a measurement method (for example the method of FIG. 20) in the management of a lithographic manufacturing system. The steps will be listed here, and then explained in more detail:

S21: Process wafer to produce structures on substrate
S22: Measure CD and/or other parameter across substrate
S23: Update metrology recipe
S24: Update lithography and/or process recipe At step S21, structures are produced across a substrate using the lithographic manufacturing system. At S22, the EUV metrology apparatus 244 and optionally other metrology apparatus and information sources are used to measure a property of the structures across the substrate. At step S23, optionally, metrology recipes and calibrations of the EUV metrology apparatus and/or other metrology apparatus 240 are updated in light of the measurement results obtained. For example, where the EUV metrology apparatus 244 has a lower throughput than the optical metrology apparatus 240, a few accurate measurements using EUV radiation can be used to improve the calculation of measurements made using the optical metrology apparatus, for a specific substrate design and process.

At step S24, measurements of CD or other parameters are compared with desired values, and used to update settings of the lithographic apparatus and/or other apparatus within the lithographic manufacturing system. By providing an EUV metrology apparatus with improved throughput, the performance of the whole system can be improved. Product features and/or product-like features can be measured directly, even at the smallest technology nodes, and in-die targets can be provided and measured without losing too much area.

In the above steps, it is assumed that sufficient targets are measured across a substrate and across multiple substrates, that statistically reliable models of the process are derivable. The profile of CD and other parameters does not need to be expressed entirely as a variation across the substrate. It can be expressed for example as an intra-field profile that is common to all fields (each instance of patterning using the patterning device M at a different location on the substrate W) and a lower order, inter-field, variation onto which the intra-field variation is repeatedly superimposed. The settings of the lithographic process adjusted in step S24 can include intra-field settings as well as inter-field settings. They may be applicable to all operations of the apparatus, or specific to a particular product layer.

Overlay Metrology by EUV Reflectometry

Particularly with reference to the examples of FIGS. 16 to 19, the methods and apparatus described herein can be applied also to the measurement of asymmetry-related features, such as overlay. Overlay between layers in a semiconductor product may be difficult to measure using EUV spectroscopic reflectometry at some incidence angles an/or wavelengths, because of the shallow penetration depth of radiation. Nevertheless, by providing the illustrated apparatus with a broad range of wavelengths (for example 1-100 nm or 1-150 nm) and with the possibility to use elevated incidence angles, practical measurements of overlay may be expected. In a multiple-patterning process, structures are formed in one layer of the product not in one patterning operation but in two or more patterning steps. Thus, for example, a first population of structures may be interleaved with a second population of structures, and the populations are formed in different steps, so as to achieve a higher resolution than one step alone can produce. While the placement of the populations should be identical and perfect in relation to other features on the substrate, of course every real pattern exhibits a certain positional offset. Any unintentional positional offset between the populations can be regarded as a form of overlay, and can be measured by asymmetry of the target grating or product features formed by multiple patterning processes. Other types of asymmetry, for example sidewall asymmetry and trench bottom asymmetry can also be measured, for a simple grating structure.

While asymmetry can be measured from (zero order) reflection spectra 310, 1410, 1710, 1910, asymmetry information will be stronger in the first order diffracted spectra 1752 and 1952 detected in the examples of FIGS. 16 to 19. Accordingly, a method of EUV metrology may include using signals SF representing first order diffraction spectra from a periodic structure to measure asymmetry in the structure. The structure may be measured in one orientation only, or it may be measured in orientations rotated (Rz) by 180°. As is known from diffraction based overlay at visible wavelengths, the asymmetry can be calculated by comparing the intensity of +1 and −1 order diffracted radiation. By rotating the target through 180°, signals SF(+1) and SF(−1) can be obtained and compared. Asymmetry can be calculated like any other property of the target, by a reconstruction method of the type described in FIG. 20. Alternatively, simpler calculations, combined with prior calibration, can be based more directly on comparing the +1 and −1 order spectra. However, using full reconstruction, in combination with the spectroscopic approach, the information available may assist a more accurate measurement than simply comparing +1 and −1 order intensities at a single wavelength. In EUV reflectometry, it is an advantage that the target can be made of product features or product-like features, which is not possible with current optical techniques using longer wavelengths. Sensitivity to overlay is expected to be greater than current tools.

Hybrid Metrology System

A hybrid metrology apparatus can be produced which includes both EUV metrology apparatus 244 for performing and optical metrology apparatus 240 for performing more conventional scatterometry measurements. Both apparatuses may work simultaneously on the same parts or different parts of a same substrate W. The two apparatuses may in practice operate at different times, while sharing common components such as substrate handling and positioning systems. The metrology apparatuses may be integrated with either the lithographic apparatus LA itself or within the lithographic cell LC.

The different apparatuses may measure different target structures, so that for example the optical metrology apparatus 240 is used to measure targets T1, while EUV metrology apparatus 244 is used to measure targets T2. Applications and benefits of such hybrid metrology techniques are disclosed in our European patent application 14168067.8, filed on 13 May 2014 [Applicant's Reference 2014P00038], not published at the present priority date.

CONCLUSION

While specific embodiments of the invention have been described above, it will be appreciated that the invention may be practiced otherwise than as described. In association with the novel targets as realized on substrates and patterning devices, an embodiment may include a computer program containing one or more sequences of machine-readable instructions describing a methods of producing targets on a substrate, measuring targets on a substrate and/or processing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein.

Further embodiments according to the invention are provided in below numbered clauses:

1. A method of measuring a property of a structure manufactured by a lithographic process, the method comprising:
   (a) irradiating a periodic structure with a beam of radiation along an irradiation direction, the periodic structure having been formed by said lithographic process on a substrate and having a periodicity in at least a first direction, the radiation comprising a plurality of wavelengths in the range of 1-100 nm, the irradiation direction being greater than 2° from a direction parallel to the substrate;
   (b) detecting a spectrum of radiation reflected by the periodic structure, and
   (c) processing signals representing the detected spectrum to determine a property of the periodic structure.

2. A method according to clause 1 wherein the beam of radiation when projected onto the periodic structure has an extent less than 10 μm, optionally less than 5 μm.

3. A method according to clause 1 or 2 wherein the beam of radiation has a minimum diameter less than 1 μm, optionally less than 500 nm.

4. A method according to clause 2 or 3 wherein the irradiation direction relative to a direction parallel to the substrate is adjusted prior to detecting said spectrum and a diameter of the beam of radiation is adjusted correspondingly to adjust the extent of beam when projected onto the periodic structure.

5. A method according to any preceding clause wherein an incidence angle, defined as the angle between the irradiation direction and a direction parallel to the substrate, is between 5° and 45°, optionally between 10° and 30°.

6. A method according to any preceding clause wherein the radiation in step (a) is a beam of radiation which is generated by focusing a source beam in both first and second dimensions.

7. A method according to clause 6 wherein the focusing in both first and second dimensions is performed using a two-dimensionally curved reflector.

8. A method according to any preceding clause wherein an illumination system used to generate the beam of radiation is housed in a vacuum environment and the substrate is held in a low-pressure gaseous environment, the low-pressure gaseous environment being defined by a housing that is openable to load and unload new substrates without disturbing the vacuum environment of the illumination system.

9. A method according to any preceding clause wherein a detection system used to detect the spectrum of the reflected radiation is housed in a vacuum environment and the substrate is held in a low-pressure gaseous environment, the low-pressure gaseous environment being defined by a housing that is openable to load and unload new substrates without disturbing the vacuum environment of the detection system.

10. A method according to any preceding clause wherein the irradiation direction defines a non-zero azimuthal angle relative to the first direction, when projected onto a plane of the substrate.

11. A method according to clause 10 wherein said azimuthal angle is selected so that a diffraction efficiency of the periodic structure in one or more non-zero diffraction orders is greater than would be the case for an irradiation direction of zero azimuthal angle.

12. A method according to clause 11 wherein the azimuthal angle is selected so that a diffraction efficiency of the periodic structure in a first order of diffraction is more than two times, optionally more than five times or more than ten times the diffraction efficiency for zero azimuthal angle.

13. A method according to according to any preceding clause wherein step (b) further includes detecting a non-zero diffraction order of radiation diffracted by the periodic structure, the non-zero diffraction order being spread into a spectrum by the periodic structure.

14. A method according to any preceding clause wherein said property is asymmetry.

15. A method according to any preceding clause wherein said property is asymmetry and the periodic structure is a grating formed in one or more layers by two or more patterning steps.

16. A method according to any of clauses 13 to 15 wherein said wherein steps (a) and (b) are performed at least twice, with the periodic structure rotated 0° and 180° about a normal axis, and wherein in step (c) signals representing the spectrum of the non-zero diffraction order under 0° and 180° rotation are used together to determine asymmetry of the periodic structure.

17. A method according to any preceding clause wherein steps (a) and (b) are repeated using different irradiation directions and wherein in step (c) signals representing the spectrum of reflected radiation detected using a plurality of different irradiation angles are used together to determine the property of the periodic structure.

18. A method according to any preceding clause wherein the step (c) includes defining a parameterized model of the periodic structure and using the model to perform performing mathematical reconstruction of the structure based on the detected reflected radiation.

19. A method according to any preceding clause wherein said property is linewidth.

20. A metrology apparatus for use in measuring performance of a lithographic process, the apparatus comprising:
an irradiation system for generating a beam of radiation, the radiation comprising a plurality of wavelengths in the range of 1-100 nm;
a substrate support operable with the irradiation system for irradiating a periodic structure formed on the substrate with radiation along an irradiation direction, the irradiation direction being greater than 2° from a direction parallel to the substrate; and
a detection system for detecting a spectrum of radiation reflected by the periodic structure.

21. An apparatus according to clause 20 wherein the beam of radiation when projected onto the periodic structure has an extent less than 10 µm, optionally less than 5 µm.

22. An apparatus according to clause 20 or 21 wherein the beam of radiation can be formed with a minimum diameter less than 1 µm, optionally less than 500 nm.

23. An apparatus according to clause 21 or 22 wherein the irradiation direction relative to a direction parallel to the substrate is adjustable and a diameter of the beam of radiation is adjustable correspondingly to adjust the extent of beam when projected onto the periodic structure.

24. An apparatus according to any of clauses 20 to 23 wherein an incidence angle, defined as the angle between the irradiation direction and a direction parallel to the substrate, can be set at least to values between 5° and 45°.

25. An apparatus according to any of clauses 20 to 24 wherein the beam of radiation is generated by focusing a source beam in both first and second dimensions.

26. An apparatus according to clause 25 wherein a two-dimensionally curved reflector is provided for focusing the beam in both first and second dimensions.

27. An apparatus according to any of clauses 20 to 26 wherein an illumination system used to generate the beam of radiation is housed in a vacuum environment and the substrate is held in a low-pressure gaseous environment, the low-pressure gaseous environment being defined by a housing that is openable to load and unload new substrates without disturbing the vacuum environment of the illumination system.

28. An apparatus according to any of clauses 20 to 27 wherein a detection system used to detect the spectrum of the reflected radiation is housed in a vacuum environment and the substrate is held in a low-pressure gaseous environment, the low-pressure gaseous environment being defined by a housing that is openable to load and unload new substrates without disturbing the vacuum environment of the detection system.

29. An apparatus according to any of clauses 20 to 28 wherein the irradiation direction defines a non-zero azimuthal angle relative to the first direction, when projected onto a plane of the substrate, and the azimuthal angle is adjustable without demounting the substrate.

30. An apparatus according to any of clauses 20 to 29 further comprising a detector for detecting a non-zero diffraction order of radiation diffracted by the periodic structure, the non-zero diffraction order being spread into a spectrum by the periodic structure.

31. An apparatus according to any of clauses 20 to 30 wherein the substrate support is adapted to receive semiconductor wafers from an automated wafer handler.

32. An apparatus according to any of clauses 20 to 31 further comprising a processing system for processing signals representing the detected reflected radiation to determine a property of the periodic structure, 33. A device manufacturing method comprising:
transferring a pattern from a patterning device onto a substrate using a lithographic process, the pattern defining at least one periodic structure;
measuring one or more properties of the periodic structure to determine a value for one or more parameters of the lithographic process; and
applying a correction in subsequent operations of the lithographic process in accordance with the measured property,
wherein the step of measuring the properties of the periodic structure includes measuring a property by a method according to any of clauses 1 to 19.

34. A device manufacturing method according to clause 33 wherein said functional device pattern defines product features having a critical dimension less than 50 nm, optionally less than 20 nm.

35. A method of measuring a property of a structure manufactured by a lithographic process, the method comprising:
(a) irradiating a periodic structure with a beam of radiation along an irradiation direction, the periodic structure having been formed by said lithographic process on a substrate and having a periodicity in at least a first direction, the radiation comprising a plurality of wavelengths in the range of 1-100 nm, the irradiation direction being greater than 2° from a direction parallel to the substrate;
(b) detecting a spectrum of radiation diffracted by the periodic structure, the non-zero diffraction order being spread into said spectrum by the periodic structure reflected by the periodic structure; and,
(c) processing signals representing the detected spectrum to determine a property of the periodic structure.

36. A method according to clause 35 wherein said property is asymmetry.

37. A method according to clause 35 or 36 wherein step (c) further comprises calculating a measure of overlay between parts of the periodic structure formed in different patterning steps.

38. A method according to clause 36 or 37 wherein the periodic structure is a grating formed in one or more layers by two or more patterning steps.

39. A method of measuring a property of a structure manufactured by a lithographic process, the method comprising:
(a) irradiating a periodic structure with a beam of radiation along an irradiation direction, the periodic structure having been formed by said lithographic process on a substrate and having a periodicity in at least a first direction, the radiation comprising a plurality of wavelengths in the range of 1-150 nm, the irradiation direction being greater than 2° from a direction parallel to the substrate;
(b) detecting a spectrum of radiation reflected by the periodic structure, and
(c) processing signals representing the detected spectrum to determine a property of the periodic structure.

40. A metrology apparatus for use in measuring performance of a lithographic process, the apparatus comprising:
an irradiation system for generating a beam of radiation, the radiation comprising a plurality of wavelengths in the range of 1-150 nm;
a substrate support operable with the irradiation system for irradiating a periodic structure formed on the substrate with radiation along an irradiation direction, the irradiation direction being greater than 2° from a direction parallel to the substrate; and
a detection system for detecting a spectrum of radiation reflected by the periodic structure.

41. A method of measuring a property of a structure manufactured by a lithographic process, the method comprising:
(a) irradiating a periodic structure with a beam of radiation along an irradiation direction, the periodic structure having been formed by said lithographic process on a substrate and having a periodicity in at least a first direction, the radiation comprising a plurality of wavelengths in the range of 1-150 nm, the irradiation direction being greater than 2° from a direction parallel to the substrate;
(b) detecting a spectrum of radiation diffracted by the periodic structure, the non-zero diffraction order being spread into said spectrum by the periodic structure reflected by the periodic structure; and,
(c) processing signals representing the detected spectrum to determine a property of the periodic structure.

Although patterning devices in the form of a physical reticle have been described, the term "patterning device" in this application also includes a data product conveying a pattern in digital form, for example to be used in conjunction with a programmable patterning device.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of measuring a property of a structure manufactured by a lithographic process, the method comprising:
   irradiating a periodic structure with a beam of radiation along an irradiation direction, the periodic structure having been formed by said lithographic process on a substrate and having a periodicity in at least a first direction, the radiation comprising a plurality of wavelengths in the range of 1-100 nm, the irradiation direction being greater than 2° from a direction parallel to the substrate, wherein the beam of radiation has a spot size of less than 10 μm on the substrate;
   detecting a spectrum of radiation reflected by the periodic structure, and
   processing signals representing the detected spectrum to determine a property of the periodic structure.

2. The method as claimed in claim 1, wherein the irradiation direction relative to a direction parallel to the substrate is adjusted prior to detecting said spectrum and a diameter of the beam of radiation is adjusted correspondingly to adjust the extent of beam when projected onto the periodic structure.

3. The method as claimed in claim 1, wherein an illumination system used to generate the beam of radiation is housed in a vacuum environment and the substrate is held in a low-pressure gaseous environment, the low-pressure gaseous environment being defined by a housing that is openable to load and unload new substrates without disturbing the vacuum environment of the illumination system.

4. The method as claimed in claim 1, wherein a detection system used to detect the spectrum of the reflected radiation is housed in a vacuum environment and the substrate is held in a low-pressure gaseous environment, the low-pressure gaseous environment being defined by a housing that is openable to load and unload new substrates without disturbing the vacuum environment of the detection system.

5. The method as claimed in claim 1, wherein the irradiation direction defines a non-zero azimuthal angle relative to the first direction, when projected onto a plane of the substrate.

6. The method as claimed in claim 1, wherein the detecting further comprises detecting a non-zero diffraction order of radiation diffracted by the periodic structure, the non-zero diffraction order being spread into a spectrum by the periodic structure.

7. The method as claimed in claim 1, wherein said property is asymmetry.

8. The method as claimed in claim 6, wherein:
   the irradiating and the detecting are performed at least twice, with the periodic structure rotated 0° and 180° about a normal axis, and
   during the processing signals representing the spectrum of the non-zero diffraction order under 0° and 180° rotation are used together to determine asymmetry of the periodic structure.

9. The method as claimed in claim 1, wherein:
   the irradiating and the detecting are repeated using different irradiation directions; and
   the processing comprises processing signals representing the spectrum of reflected radiation detected using a plurality of different irradiation angles to determine the property of the periodic structure.

10. The method as claimed in claim 1, wherein the processing includes defining a parameterized model of the periodic structure and using the model to perform mathematical reconstruction of the structure based on the detected reflected radiation.

11. A metrology apparatus for use in measuring performance of a lithographic process, the apparatus comprising:
    an irradiation system configured to generate a beam of radiation, the radiation comprising a plurality of wavelengths in the range of 1-100 nm;
    a substrate support configured to support a substrate and operable with the irradiation system to irradiate a periodic structure formed on the substrate with the beam of radiation along an irradiation direction, the irradiation direction being greater than 2° from a direction parallel to the substrate, wherein the beam of radiation has a spot size of less than 10 μm on the substrate; and
    a detection system configured to detect a spectrum of radiation reflected by the periodic structure.

12. The apparatus as claimed in claim 11, wherein the irradiation direction relative to a direction parallel to the substrate is adjustable and a diameter of the beam of radiation is adjustable correspondingly to adjust the extent of beam when projected onto the periodic structure.

13. The apparatus as claimed in claim 11, wherein an illumination system used to generate the beam of radiation is housed in a vacuum environment and the substrate is held in a low-pressure gaseous environment, the low-pressure gaseous environment being defined by a housing that is openable to load and unload new substrates without disturbing the vacuum environment of the illumination system.

14. The apparatus as claimed in claim 11, wherein a detection system used to detect the spectrum of the reflected radiation is housed in a vacuum environment and the substrate is held in a low-pressure gaseous environment, the low-pressure gaseous environment being defined by a housing that is openable to load and unload new substrates without disturbing the vacuum environment of the detection system.

15. The apparatus as claimed in claim 11, wherein the irradiation direction defines a non-zero azimuthal angle relative to the first direction, when projected onto a plane of the substrate, and the azimuthal angle is adjustable without demounting the substrate.

16. The apparatus as claimed in claim 11, further comprising a detector configured to detect a non-zero diffraction order of radiation diffracted by the periodic structure, the non-zero diffraction order being spread into a spectrum by the periodic structure.

17. The apparatus as claimed in claim 11, wherein the substrate support is adapted to receive semiconductor wafers from an automated wafer handler.

18. The apparatus as claimed in claim 11, further comprising a processing system configured to process signals representing the detected reflected radiation to determine a property of the periodic structure.

19. A device manufacturing method comprising:
    transferring a pattern from a patterning device onto a substrate using a lithographic process, the pattern defining at least one periodic structure;

measuring one or more properties of the periodic structure to determine a value for one or more parameters of the lithographic process; and applying a correction in subsequent operations of the lithographic process in accordance with the measured property, wherein the step of measuring the properties of the periodic structure includes measuring a property by a method comprising:

irradiating a periodic structure with a beam of radiation along an irradiation direction, the periodic structure having been formed by said lithographic process on a substrate and having a periodicity in at least a first direction, the radiation comprising a plurality of wavelengths in the range of 1-100 nm, the irradiation direction being greater than 2° from a direction parallel to the substrate, wherein the beam of radiation has a spot size of less than 10 µm on the substrate;

detecting a spectrum of radiation reflected by the periodic structure, and processing signals representing the detected spectrum to determine a property of the periodic structure.

20. A method of measuring a property of a structure manufactured by a lithographic process, the method comprising:

irradiating a periodic structure with a beam of radiation along an irradiation direction, the periodic structure having been formed by said lithographic process on a substrate and having a periodicity in at least a first direction, the radiation comprising a plurality of wavelengths in the range of 1-100 nm, the irradiation direction being greater than 2° from a direction parallel to the substrate, wherein the beam of radiation has a spot size of less than 10 µm on the substrate;

detecting a spectrum of radiation diffracted by the periodic structure, wherein a non-zero diffraction order of the radiation is spread into said spectrum by the periodic structure; and, processing signals representing the detected spectrum to determine a property of the periodic structure.

21. The method as claimed in claim 1, wherein the beam of radiation has a spot size of less than 5 µm on the substrate.

22. The apparatus as claimed in claim 11, wherein the beam of radiation has a spot size of less than 5 µm on the substrate.

\* \* \* \* \*